(12) United States Patent
Palmer et al.

(10) Patent No.: US 10,687,965 B2
(45) Date of Patent: *Jun. 23, 2020

(54) MICROPROCESSOR CONTROLLED PROSTHETIC ANKLE SYSTEM FOR FOOTWEAR AND TERRAIN ADAPTATION

(71) Applicant: FREEDOM INNOVATIONS, LLC, Irvine, CA (US)

(72) Inventors: Michael L. Palmer, Ladera Ranch, CA (US); Matt McFadden, Irvine, CA (US); Hugo Quintero, Irvine, CA (US)

(73) Assignee: Freedom Innovations, LLC, Irvine, CA (US)

( * ) Notice: Subject to any disclaimer, the term of this patent is extended or adjusted under 35 U.S.C. 154(b) by 87 days.

This patent is subject to a terminal disclaimer.

(21) Appl. No.: 15/832,513

(22) Filed: Dec. 5, 2017

(65) Prior Publication Data

US 2018/0256371 A1    Sep. 13, 2018

Related U.S. Application Data

(63) Continuation of application No. 14/466,122, filed on Aug. 22, 2014, now Pat. No. 9,849,002.

(Continued)

(51) Int. Cl.
*A61F 2/66* (2006.01)
*A61F 2/68* (2006.01)
(Continued)

(52) U.S. Cl.
CPC .............. *A61F 2/6607* (2013.01); *A61F 2/68* (2013.01); *A61F 2002/5006* (2013.01);
(Continued)

(58) Field of Classification Search
CPC .. A61F 2/66; A61F 2/68; A61F 2/6607; A61F 2002/5006; A61F 2002/745; A61F 2/60
See application file for complete search history.

(56) References Cited

U.S. PATENT DOCUMENTS

| 2,465,585 A | 3/1947 | Ganoe et al. |
| 2,470,480 A | 5/1949 | Fogg |

(Continued)

FOREIGN PATENT DOCUMENTS

| DE | 811714 C | 8/1951 |
| DE | 4410730 C1 | 6/1995 |

(Continued)

OTHER PUBLICATIONS

Bloch, Heinz, (Dec. 18, 2005). "Pump Repair and Restoration Guidelines", Chemical Processing Industry News, 8 pages.

(Continued)

*Primary Examiner* — Marcia L Watkins
(74) *Attorney, Agent, or Firm* — Dorsey & Whitney LLP

(57) ABSTRACT

A prosthetic ankle includes a pair of prosthetic members movably coupled together to allow movement of the pair of prosthetic members with respect to one another. A hydraulic actuator or damper including hydraulic fluid in a hydraulic chamber is coupled to one of the pair of prosthetic members. A hydraulic piston is movably disposed in the hydraulic chamber and coupled to another of the pair of prosthetic members. A hydraulic flow channel is fluidly coupled between opposite sides of the chamber to allow hydraulic fluid to move between the opposite sides of the chamber as the hydraulic piston moves therein. A voice coil valve is coupled to the hydraulic flow channel to vary resistance to flow of hydraulic fluid through the flow channel, and thus movement of the piston in the chamber, and thus influencing a rate of movement of the pair of prosthetic members with respect to one another.

14 Claims, 19 Drawing Sheets

Related U.S. Application Data

(60) Provisional application No. 61/870,704, filed on Aug. 27, 2013.

(51) Int. Cl.
*A61F 2/70* (2006.01)
*A61F 2/74* (2006.01)
*A61F 2/76* (2006.01)
*A61F 2/50* (2006.01)

(52) U.S. Cl.
CPC ............ *A61F 2002/5032* (2013.01); *A61F 2002/5033* (2013.01); *A61F 2002/5035* (2013.01); *A61F 2002/5043* (2013.01); *A61F 2002/5073* (2013.01); *A61F 2002/5084* (2013.01); *A61F 2002/6614* (2013.01); *A61F 2002/6657* (2013.01); *A61F 2002/6854* (2013.01); *A61F 2002/6863* (2013.01); *A61F 2002/701* (2013.01); *A61F 2002/704* (2013.01); *A61F 2002/707* (2013.01); *A61F 2002/708* (2013.01); *A61F 2002/74* (2013.01); *A61F 2002/741* (2013.01); *A61F 2002/745* (2013.01); *A61F 2002/748* (2013.01); *A61F 2002/764* (2013.01); *A61F 2002/7625* (2013.01); *A61F 2002/7635* (2013.01); *A61F 2002/7645* (2013.01)

(56) References Cited

U.S. PATENT DOCUMENTS

| | | |
|---|---|---|
| 2,843,853 A | 7/1958 | Mauch |
| 3,053,236 A | 9/1962 | Self et al. |
| 3,457,956 A | 7/1969 | Andrews |
| 3,457,959 A | 7/1969 | Cooper |
| 3,749,128 A | 7/1973 | Sallberg et al. |
| 3,871,032 A | 3/1975 | Karas |
| 4,134,424 A | 1/1979 | Zeyra et al. |
| 4,838,392 A | 6/1989 | Miller et al. |
| 5,092,902 A | 3/1992 | Adams et al. |
| 5,246,465 A | 9/1993 | Rincoe et al. |
| 5,290,319 A | 3/1994 | Phillips |
| 5,383,939 A | 1/1995 | James |
| 5,544,528 A | 8/1996 | Woyski et al. |
| 5,571,205 A | 11/1996 | James |
| 5,586,435 A | 12/1996 | Kokalis |
| 5,810,130 A | 9/1998 | McCandless |
| 5,888,212 A | 3/1999 | Petrofsky et al. |
| 5,893,891 A | 4/1999 | Zahedi |
| 5,921,358 A | 7/1999 | Gramnas |
| 5,957,981 A | 9/1999 | Gramnas |
| 6,007,582 A | 12/1999 | May |
| 6,082,507 A | 7/2000 | Forster |
| 6,113,642 A | 9/2000 | Petrofsky et al. |
| 6,427,970 B1 | 8/2002 | Silva |
| 6,443,993 B1 | 9/2002 | Koniuk |
| 6,517,585 B1 | 2/2003 | Zahedi et al. |
| 6,673,117 B1 | 1/2004 | Soss et al. |
| 6,719,807 B2 | 4/2004 | Harris |
| 6,740,125 B2 | 5/2004 | Mosler |
| 6,741,911 B2 | 5/2004 | Simmons |
| 6,755,870 B1 | 6/2004 | Biedermann et al. |
| 6,764,520 B2 | 7/2004 | Deffenbaugh et al. |
| 6,855,170 B2 | 2/2005 | Gramnas |
| 6,875,241 B2 | 4/2005 | Christesen |
| 6,902,585 B2 | 6/2005 | Hikichi |
| 6,910,331 B2 | 6/2005 | Asai et al. |
| 6,911,050 B2 | 6/2005 | Molino et al. |
| 7,052,519 B1 | 5/2006 | Gramnas |
| 7,066,964 B2 | 6/2006 | Wild |
| 7,279,009 B2 | 10/2007 | Herr et al. |
| RE39,961 E | 12/2007 | Petrofsky et al. |
| 7,393,364 B2 | 7/2008 | Martin |
| 7,485,152 B2 | 2/2009 | Haynes et al. |
| 7,507,259 B2 | 3/2009 | Townsend et al. |
| 7,655,050 B2 | 2/2010 | Palmer et al. |
| 7,691,154 B2 | 4/2010 | Asgeirsson et al. |
| 7,799,091 B2 | 9/2010 | Herr et al. |
| 7,845,370 B2 | 12/2010 | Cook et al. |
| 7,848,058 B2 | 12/2010 | Huang et al. |
| 7,862,622 B2 | 1/2011 | Dunlap et al. |
| 7,883,548 B2 | 2/2011 | Lang |
| 7,942,935 B2 | 5/2011 | Iversen et al. |
| 7,963,998 B2 | 6/2011 | Boiten |
| 7,985,265 B2 | 7/2011 | Moser et al. |
| 8,001,993 B2 | 8/2011 | Cook |
| 8,142,370 B2 | 3/2012 | Weinberg et al. |
| 8,206,458 B1 | 6/2012 | Hawkins |
| 8,444,704 B2 | 5/2013 | Palmer et al. |
| 8,574,312 B2 | 11/2013 | Moser et al. |
| 8,623,098 B2 | 1/2014 | Goldfarb et al. |
| 8,641,780 B2 | 2/2014 | Abimosleh et al. |
| 8,652,218 B2 | 2/2014 | Goldfarb et al. |
| 8,655,808 B2 | 2/2014 | Palmer et al. |
| 8,740,991 B2 | 6/2014 | Moser et al. |
| 8,959,038 B2 | 2/2015 | Palmer et al. |
| 8,986,389 B2 | 3/2015 | Lim et al. |
| 8,986,396 B2 | 3/2015 | Goldfarb et al. |
| 8,986,398 B2 | 3/2015 | Poulson, III et al. |
| 9,028,557 B2 | 5/2015 | Steele et al. |
| 9,180,025 B2 | 11/2015 | Goldfarb et al. |
| 9,289,315 B2 | 3/2016 | Goldfarb et al. |
| 9,289,317 B2 | 3/2016 | Goldfarb et al. |
| 9,750,620 B2 | 9/2017 | Goldfarb et al. |
| 9,763,809 B2 | 9/2017 | Palmer et al. |
| 9,849,002 B2 | 12/2017 | Palmer et al. |
| 2002/0152750 A1 | 10/2002 | Asai et al. |
| 2005/0092952 A1 | 5/2005 | McCarroll et al. |
| 2006/0235544 A1 | 10/2006 | Iversen et al. |
| 2006/0293761 A1 | 12/2006 | Baumann et al. |
| 2007/0050044 A1 | 3/2007 | Haynes et al. |
| 2007/0061016 A1 | 3/2007 | Kuo et al. |
| 2007/0083272 A1 | 4/2007 | Van De Veen et al. |
| 2007/0198098 A1 | 8/2007 | Roston et al. |
| 2008/0097269 A1 | 4/2008 | Weinberg et al. |
| 2008/0099090 A1 | 5/2008 | Cook |
| 2008/0114272 A1 | 5/2008 | Herr et al. |
| 2008/0200994 A1 | 8/2008 | Colgate et al. |
| 2008/0262635 A1 | 10/2008 | Moser et al. |
| 2008/0281435 A1 | 11/2008 | Abimosleh et al. |
| 2008/0300692 A1 | 12/2008 | Moser et al. |
| 2009/0001305 A1 | 1/2009 | Cook et al. |
| 2009/0030530 A1 | 1/2009 | Martin |
| 2009/0054996 A1 | 2/2009 | Sykes et al. |
| 2009/0204230 A1 | 8/2009 | Kaltenborn et al. |
| 2009/0222105 A1 | 9/2009 | Clausen |
| 2009/0259320 A1 | 10/2009 | Andrysek |
| 2009/0299489 A1 | 12/2009 | Gramnaes |
| 2010/0023133 A1 | 1/2010 | Fairbanks et al. |
| 2010/0049334 A1 | 2/2010 | Okuda et al. |
| 2010/0191347 A1 | 7/2010 | Pusch et al. |
| 2010/0292807 A1 | 11/2010 | Velez et al. |
| 2011/0082566 A1 | 4/2011 | Herr et al. |
| 2011/0087339 A1 | 4/2011 | Pusch et al. |
| 2011/0093089 A1 | 4/2011 | Martin |
| 2011/0098828 A1 | 4/2011 | Balboni et al. |
| 2011/0130846 A1 | 6/2011 | Kampas et al. |
| 2011/0197682 A1 | 8/2011 | Palmer |
| 2011/0199101 A1 | 8/2011 | Steele |
| 2011/0202144 A1 | 8/2011 | Palmer et al. |
| 2011/0224803 A1 | 9/2011 | Goldfarb et al. |
| 2011/0264230 A1 | 10/2011 | Herr et al. |
| 2011/0307078 A1 | 12/2011 | Boender |
| 2012/0004736 A1 | 1/2012 | Goldfarb et al. |
| 2012/0130508 A1 | 5/2012 | Harris et al. |
| 2012/0136458 A1 | 5/2012 | Martin |
| 2013/0268090 A1 | 10/2013 | Goldfarb et al. |
| 2013/0310949 A1 | 11/2013 | Goldfarb et al. |
| 2014/0100667 A1 | 4/2014 | Goldfarb et al. |
| 2014/0172120 A1 | 6/2014 | Steele et al. |
| 2014/0277581 A1 | 9/2014 | Steele et al. |
| 2015/0066154 A1 | 3/2015 | Palmer, III et al. |
| 2015/0066155 A1 | 3/2015 | Haque |

(56) References Cited

U.S. PATENT DOCUMENTS

| | | |
|---|---|---|
| 2015/0209159 A1 | 7/2015 | Goldfarb et al. |
| 2015/0297364 A1 | 10/2015 | Goldfarb et al. |
| 2015/0320574 A1 | 11/2015 | Steele et al. |
| 2016/0242936 A1 | 8/2016 | Goldfarb et al. |
| 2016/0287414 A1 | 10/2016 | Goldfarb et al. |
| 2017/0100264 A1 | 4/2017 | Goldfarb et al. |
| 2017/0333222 A1 | 11/2017 | Goldfarb et al. |

FOREIGN PATENT DOCUMENTS

| | | |
|---|---|---|
| EP | 0 576 379 A1 | 12/1993 |
| EP | 1 101 461 A1 | 5/2001 |
| GB | 2 138 969 A | 10/1984 |
| GB | 2 367 753 A | 4/2002 |
| JP | 59-183747 A1 | 10/1984 |
| JP | 5336386 B2 | 11/2013 |
| WO | WO-02/15826 A1 | 2/2002 |
| WO | WO 2011/080556 A2 | 7/2011 |
| WO | WO 2011/080556 A3 | 7/2011 |

OTHER PUBLICATIONS

Corrected Notice of Allowability dated Aug. 23, 2017, for U.S. Appl. No. 14/466,081, filed Aug. 22, 2014, 4 pages.
Custom Sensor Technologies, Verified by the Wayback Machine Nov. 14, 2012. Kimco Magnetics Voice Coil Actuators Applications and Product Selection Guide, 20 pages.
"Echelon" (Jun. 24, 2013). Located at http://www.endolite.com/products/echelon; Accessed Jun. 24, 2013; 2 Pages.
"Elan," (Jun. 24, 2013). Located at http://www.endolite.com/products/elan; Accessed Jun. 24, 2013; 2 Pages.
"Elan Flyer," (Sep. 2015). Located at http://www.endolite.com/catalogue/feet/new-elan/flyer/en_US/936562%20Elan%20Flyer%20iss5%20US_AW_web.pdf, accessed on Mar. 31, 2016, 4 pages.
Extended European Search Report dated Mar. 21, 2014, for EP Application No. 14 151 179.0, filed on Jan. 14, 2014, 9 pages.
Extended European Search Report dated Apr. 7, 2014, for EP Application No. 14 152 194.8, filed on Jan. 22, 2014, 5 pages.
Extended European Search Report dated Apr. 29, 2015, for EP Application No. 14 182 396.3, filed on Aug. 27, 2014, 9 pages.
Extended European Search Report dated Nov. 24, 2017, for EP Application No. 17 169 149.6, filed on Jan. 22, 2014, 7 pages.
Extended European Search Report dated Jan. 22, 2018, for EP Application No. 17 164 872.8, filed on Aug. 27, 2014, 6 pages.
Final Office Action dated Nov. 21, 2014, for U.S. Appl. No. 13/829,714, filed Mar. 14, 2013, 20 pages.
Final Office Action dated Jan. 12, 2017, for U.S. Appl. No. 14/466,081, filed Aug. 22, 2014, 20 pages.
Freedom Innovations; Plie$^{2.0}$ MPC Knee, trademark of Freedom Innovations, LLC; Natural by Design, 6 pages.
Korane, K. (Jun. 9, 2011). "New surface-inspection techniques improve hydraulic cylinder rods and seals," Machine Design, Penton Media, Inc., 4 pages.
Krips, W. (Jun. 1, 2003). Neue Antriebstechnolgie bei hochdynamischen Stetigwegeventilen; O+ P Olhydraulik und Pneumatik 47(6):3, Vereinigte Fachverlage; Mainz, DE; Article submitted with Parker Press Report DF Plus which reports on the technology contained in the German article, 8 total pages (with English Translation).
Laurenson (Feb. 1985). "The Design of Self-Centering Seal-Less Hydraulic Pistons," *Journal of Engineering Manufacture* 199(1):59-65 (English abstract only).
Non-Final Office Action dated Jul. 18, 2014, for U.S. Appl. No. 13/829,714, filed Mar. 14, 2013, 22 pages.
Non-Final Office Action dated Aug. 8, 2014, for U.S. Appl. No. 13/793,892, filed Mar. 11, 2013, 16 pages.
Non-Final Office Action dated Nov. 4, 2015, for U.S. Appl. No. 14/466,122, filed Aug. 22, 2014, 18 pages.
Non-Final Office Action dated May 5, 2016, for U.S. Appl. No. 14/466,081, filed Aug. 22, 2014, 16 pages.
Non-Final Office Action dated Aug. 29, 2016, for U.S. Appl. No. 14/466,122, filed Aug. 22, 2014, 13 pages.
Non-Final Office Action dated May 17, 2017, for U.S. Appl. No. 14/707,957, filed May 8, 2015, 23 pages.
Notice of Allowance dated Jan. 20, 2015, for U.S. Appl. No. 13/793,892, filed Mar. 11, 2013, 7 pages.
Notice of Allowance dated Feb. 17, 2015, for U.S. Appl. No. 13/793,892, filed Mar. 11, 2013, 4 pages.
Notice of Allowance dated May 3, 2017, for U.S. Appl. No. 14/466,081, filed Aug. 22, 2014, 8 pages.
Notice of Allowance dated Apr. 1, 2015, for U.S. Appl. No. 13/829,714, filed Mar. 14, 2013, 8 pages.
Notice of Allowance dated Aug. 16, 2017, for U.S. Appl. No. 14/466,122, filed Aug. 22, 2014, 5 pages.
Parker, "Fluid Power Seal Design Guide", Nov. 12, 2012, copyright date 2003, 8 pages.
Partial European Search Report dated Dec. 19, 2014, for EP Application No. 14 182 396.3, filed on Aug. 27, 2014, 6 pages.
Shields et al. (2006). Design, Control, and Energetic Characterization of a Solenoid Injected Monopropellant Powered Actuator; IEEE/ASME Transactions on Mechatronics 11(4):477-487.
Weingarten, F. (2004). Hyraulikosungen fur Produktions machinen; O+ P Olhydraulik und Pneumatik 48(9):1-2, Vereinigte Fachverlage; Mainz, DE. (with English Abstract).
Extended European Search Report received in EP Application No. 19160401.6 dated Aug. 29, 2019.

open flexible open flexible closed rigid open flexible closed rigid open flexible

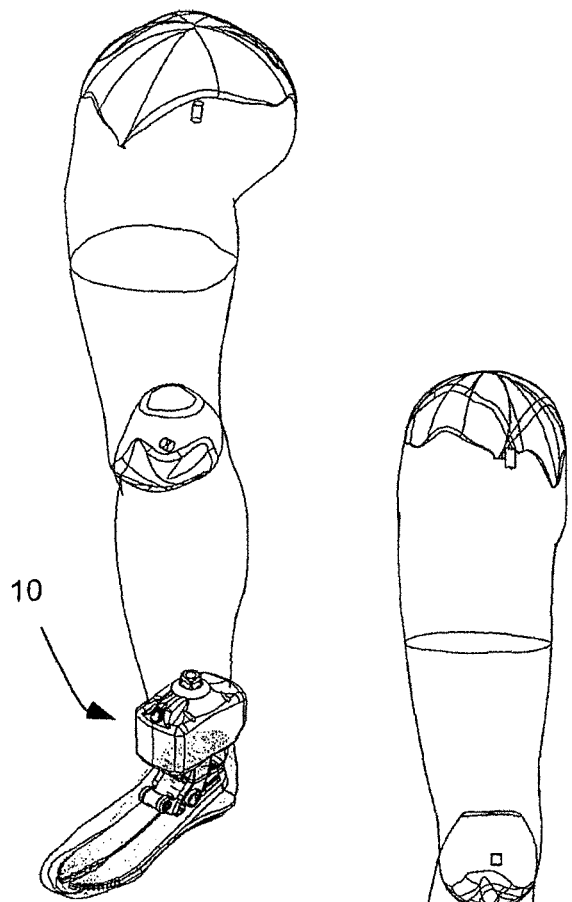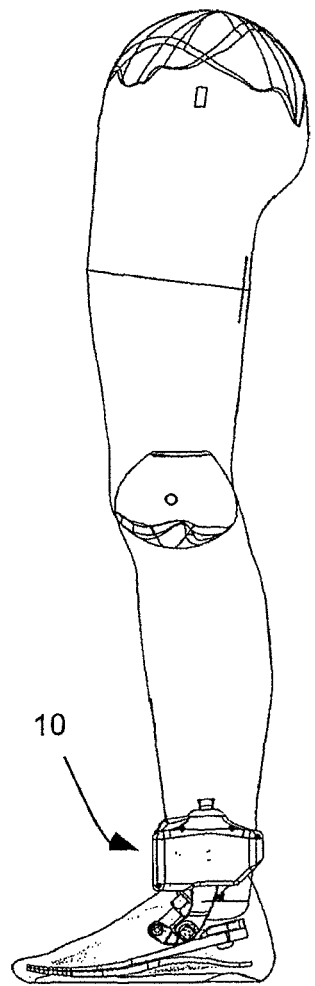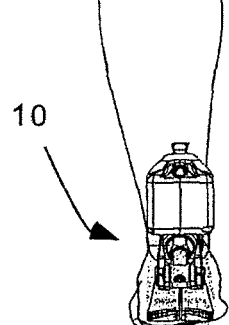
*Fig. 12a*
*Fig. 12b*
*Fig. 12c*

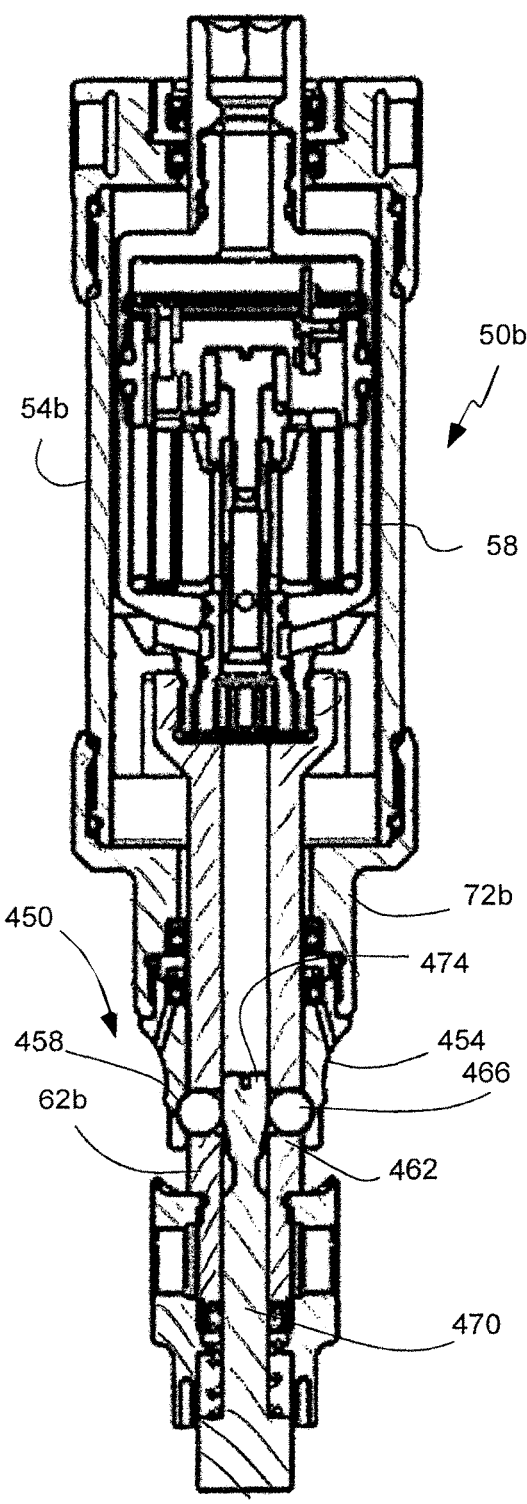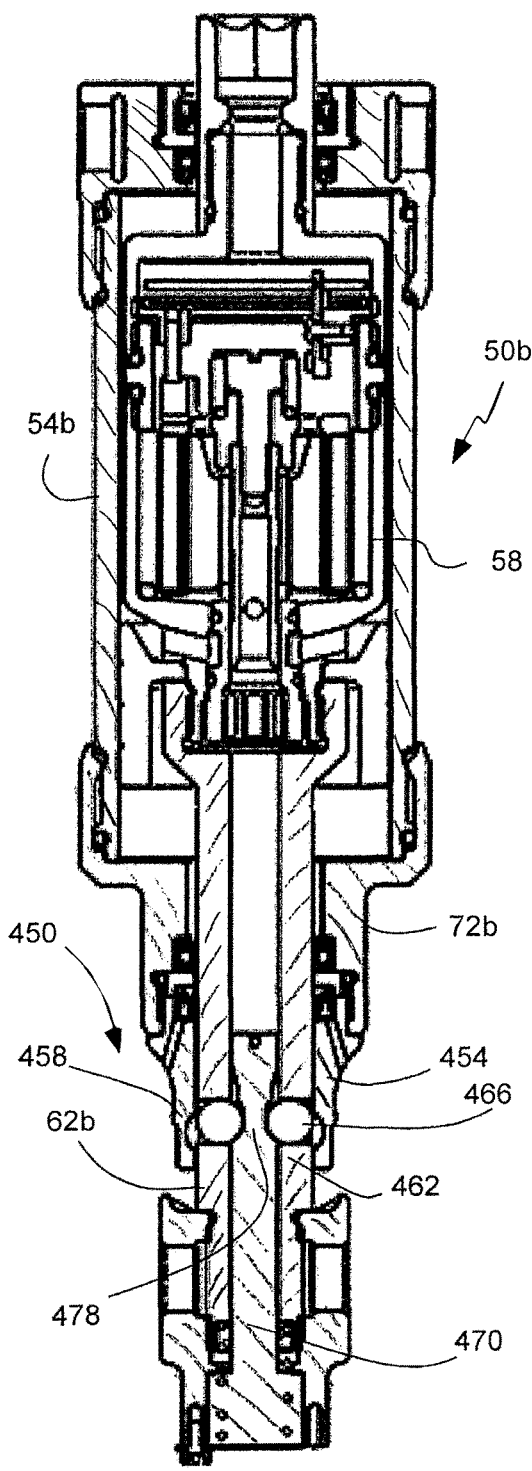
Fig. 17c
locked
Fig. 17d
unlocked

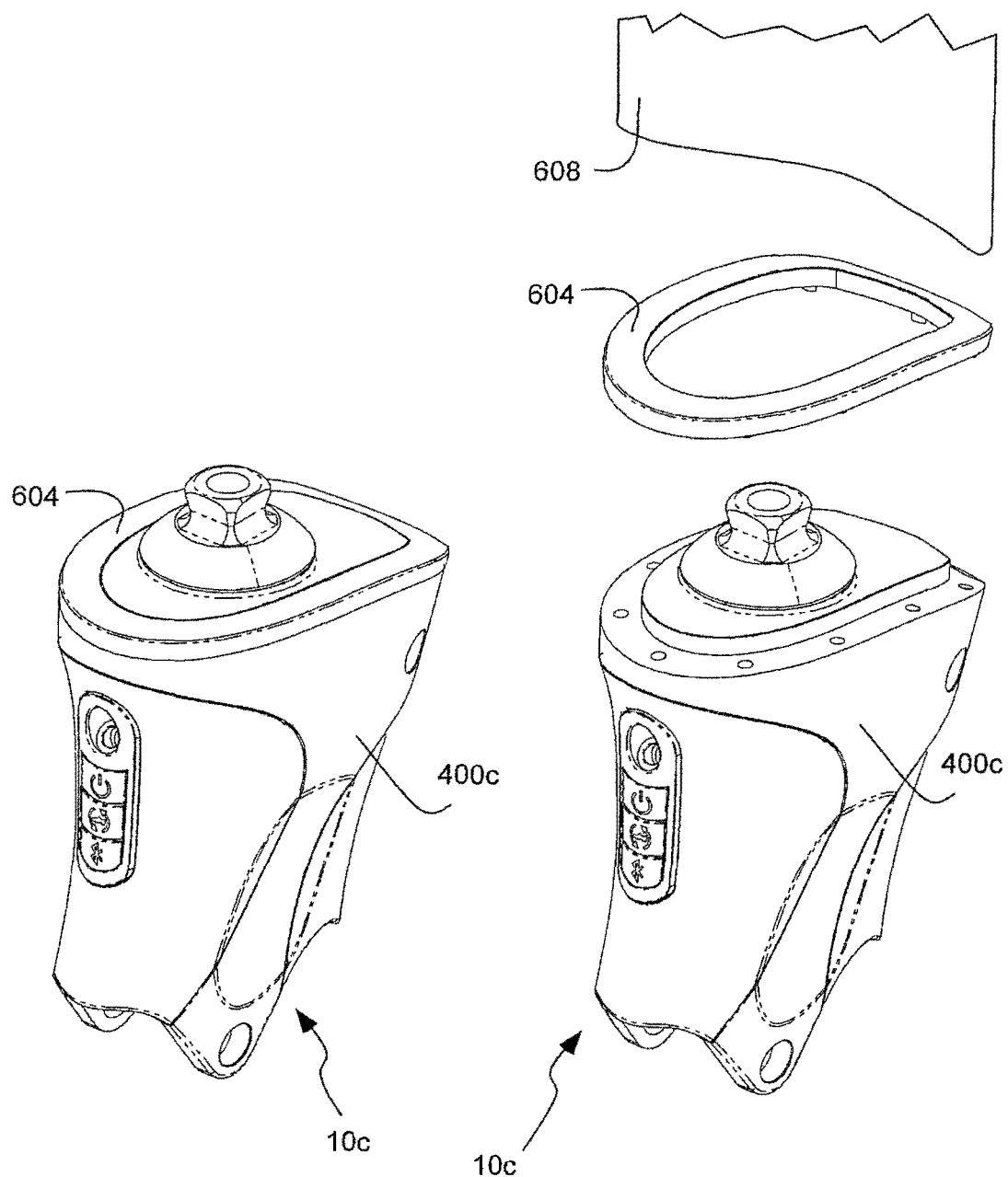
*Fig. 18a*  *Fig. 18b*

MICROPROCESSOR CONTROLLED PROSTHETIC ANKLE SYSTEM FOR FOOTWEAR AND TERRAIN ADAPTATION

RELATED APPLICATION(S)

This application is a continuation application of U.S. patent application Ser. No. 14/466,122, filed Aug. 22, 2014, which issued as U.S. Pat. No. 9,849,002 on Dec. 26, 2017, and which claims priority to U.S. Provisional Patent Application No. 61/870,704, filed Aug. 27, 2013, each of which is hereby incorporated herein by reference.

RELATED APPLICATION(S)

This is related to U.S. patent application Ser. No. 13/829,714, filed Mar. 14, 2013, and entitled "Prosthetic with Voice Coil Valve"; which is hereby incorporated herein by reference.

This is related to U.S. patent application Ser. No. 13/793,892, filed Mar. 11, 2013, and entitled "Hydraulic Prosthetic Ankle", which claims priority to U.S. Provisional Patent Application Ser. No. 61/761,003, filed Feb. 5, 2013; which are hereby incorporated herein by reference.

This is related to U.S. Pat. No. 8,746,080 (application Ser. No. 13/015,423, filed on Jan. 27, 2011), and entitled "Compact and Robust Load and Moment Sensor", which claims priority to U.S. Provisional Application Ser. No. 61/304,367, filed Feb. 12, 2010; which are hereby incorporated herein by reference.

BACKGROUND

Field of the Invention

The present invention relates generally to prosthetics with a hydraulic damper or actuator. More particularly, the present invention relates to a prosthetic ankle.

Related Art

The development of a prosthetic ankle with a more natural function or gait is an ongoing endeavor. Examples of prosthetic ankles include U.S. Pat. No. 6,443,993 (Koniuk); U.S. Pat. No. 2,843,853 (Mauch); and U.S. Pat. No. 7,985,265 (Moser). Prosthetic ankles can incorporate a hydraulic damping scheme to limit or control movement about the ankle, and/or to allow limited range of motion for the foot to provide a natural gait on slops or inclined surfaces. The hydraulic damping systems often utilize a solenoid valve to limit or resist the flow of hydraulic fluid. A solenoid valve is typically on or off, and can typically operate by drawing a plunger into an activated magnetic coil and against a spring, which spring can return the plunger when the coil is deactivated. In addition, some hydraulic damping systems may also, or in the alternative, utilize a stepper motor. Furthermore, some hydraulic damping systems can utilize a magneto rheological fluid. Alternatively, some hydraulic damping systems can utilize mechanical controls.

In addition, side loads are commonplace in prosthetic devices. Side loads cause, at a minimum, premature failure of hydraulic cylinder seals, and at the worst, binding or bending of the cylinder components, especially the shaft. The typical approach to eliminate side loads on a hydraulic cylinder is to mount it with spherical ball joints (also known as Heim joints) at both ends. In this way, side loads are not transmitted to the cylinder because the spherical ball joints move to accommodate the side loads. In prosthetic devices, using spherical ball joints can be impractical because this greatly increases the eye-to-eye length of the cylinder, but the cylinder must fit within the anatomical envelope of a natural leg. For this reason, most prosthetic devices that employ a hydraulic cylinder have the cylinder mounted on trunnions. But trunnions will transmit side loads.

Prior art prosthetic ankles often do not meet the advanced demands needed by today's amputee.

SUMMARY OF THE INVENTION

It has been recognized that it would be advantageous to develop a prosthetic foot that can provide a limited range of motion of the foot about an ankle joint that provides a more natural gait and/or feel.

In addition, it has been recognized that prior art solenoid valves in hydraulic prosthetics lack an ability to finely adjust rates of fluid flow; and that prior art stepper motor control valves in hydraulic prosthetics lack response time to control fluid in both directions, often resulting in parallel systems with double the weight and complexity. It has been recognized that it would be advantageous to develop a prosthesis, and namely an ankle prosthesis or prosthetic ankle, and/or a hydraulic damper or actuator for such prosthesis, and/or a control valve for such a prosthesis or hydraulic system, that provides bi-directional positioning, proportional control, rapid response and/or low power consumption.

In addition, it has been recognized that it would be advantageous to incorporate a voice coil valve, rather than a solenoid valve, into a prosthetic ankle, and to address size issues that such a voice coil valve may raise. Furthermore, it has been recognized that a voice coil valve can provide reciprocal or bidirectional movement based on the polarity of an applied current (as opposed to the unidirectionally driven movement in that the armature of a solenoid that only moves in one direction regardless of the polarity of the current applied, and that requires a spring for return movement). It has further been recognized that the force produced by the voice coil actuator is proportional (and substantially linear) to the current applied (and the velocity of the coil is proportional to the voltage applied), unlike a solenoid (with non-linear time and force response, and higher power consumption towards one end of the stroke due to the need of constantly working against the return spring force). Thus, the actuator has a substantially linear time and force response. The movement and force of the voice coil motor is based on the Lorentz Force principle and equation, unlike a spring returned solenoid.

In addition, it has been recognized that it would be advantageous to develop a prosthetic ankle to reduce or eliminate failure of hydraulic cylinder seals, and binding or bending of other cylinder components, such as the shaft. It has been recognized that it would be advantageous to develop a prosthetic ankle to accommodate side loads while reducing or maintaining the length of the cylinder.

In addition, it has been recognized that it would be advantageous to develop a prosthetic ankle that can change the position (ankle position or relative angle between the foot and the shank link) at which hydraulic resistance is applied by a control algorithm. It has been recognized that it would be advantageous to develop a prosthetic ankle which can lock the position of the hydraulic cylinder based on the patient's preference, the heel height of the current footwear, and/or the slop of the terrain.

In addition, it has been recognized that it would be advantageous to develop a prosthetic ankle that can utilize a wireless connection between the prosthesis and a user interface to allow the patient to move freely. In addition, it has been recognized that it would be advantageous to utilize a user interface or application software along with the wireless connection between the interface and the prosthesis that initiates a session that, if interrupted by an interruption in the wireless connection, would allow the session to resume when the wireless connection is reestablished.

In addition, it has been recognized by the inventors of the present invention that it would be advantageous to mechanically lock a hydraulic ankle. The present inventors have recognized that a hydraulic ankle with a large range of motion (e.g. 30 degrees), while providing many advantages (such as comfort while sitting, the ability to use footwear with high heels, the ability to go up and down steep hills or ramps, etc.), also can pose a safety risk. The mechanical lock that can be engaged by the patient mitigates safety risks. The mechanical lock can be used to improve safety in the case of a system failure such as a dead battery, a broken wire, etc. It can also be used to improve safety in situations where the patient would not want any unexpected ankle motion to occur, such as driving a car, climbing a ladder, etc. In addition to improved safety, the mechanical lock can also provide convenience for the clinician. The clinician can lockout the ankle during dynamic alignment of the prosthetic leg using the mechanical lock. This allows the clinician to focus on the alignment without having to worry about the hydraulic settings at the same time.

Furthermore, it has been recognized that it would be advantageous to develop a prosthetic ankle with a hydraulic system that can quickly return fluid to a main oil chamber through a low resistance path of a check valve once a high pressure event is over to insure that the high pressure event does not cause a long-term "dead band" in the cylinder because the cylinder has effectively lost fluid from the main oil chamber into the IFP chamber.

The invention provides a prosthetic ankle with a pair of prosthetic members, comprising a shank link configured to be coupled to a remnant limb of an amputee and an artificial foot, movably coupled together to allow movement of the pair of prosthetic members with respect to one another. A hydraulic actuator or damper includes a hydraulic fluid in a hydraulic chamber coupled to one of the pair of prosthetic members; and a hydraulic piston movably disposed in the hydraulic chamber and coupled to another of the pair of prosthetic members. A hydraulic flow channel is fluidly coupled between opposite sides of the chamber to allow hydraulic fluid to move between the opposite sides of the chamber as the hydraulic piston moves therein. A voice coil valve is coupled to the hydraulic flow channel to vary resistance to flow of hydraulic fluid through the flow channel, and thus movement of the piston in the chamber, and thus influencing a rate of movement of the pair of prosthetic members with respect to one another In accordance with a more detailed aspect of the present invention, the voice coil valve can open or close flow of hydraulic fluid through the flow channel, and thus allow or disallow movement of the piston in the chamber, and thus unlock or lock movement of the pair of prosthetic members with respect to one another.

In accordance with another more detailed aspect of the present invention, the artificial foot can be pivotally coupled to the shank link. A flexure can mount the hydraulic actuator or damper to the shank link or the artificial foot, and having a high stiffness in a direction parallel to a line-of-action of the hydraulic chamber to effectively transmit forces to and from the chamber, and having a low stiffness in at least one direction perpendicular to the line-of-action to resist side loads from being transmitted to the chamber.

In accordance with a more detailed aspect of the present invention, a flexure based foot coupler mount can be attached to the artificial foot, and coupled between the artificial foot and the shank link, and coupled between the artificial foot and the hydraulic actuator or damper. A single-axis pivot can be in the foot coupler mount about which the shank link and the artificial foot pivot with respect to one another. A hydraulic pivot can be in the foot coupler mount about which the hydraulic chamber or piston pivots with respect to the artificial foot. A flexure can be in the foot coupler mount between the pivots, and can be capable of flexing under an applied force or torque to center the hydraulic chamber or piston to the shank link.

In accordance with another more detailed aspect of the present invention, the prosthetic ankle can include a housing carried by the shank link and surrounding at least a portion of the shank link. A control system can be disposed in the housing. A battery can be electrically coupled to the control system and disposed in the housing. The housing, with the control system and the battery therein, can be disposed in an anatomical envelop of a natural leg. The housing, the shank link and the hydraulic actuator or damper can be disposed in the anatomical envelop of a natural leg.

In accordance with another more detailed aspect of the present invention, the shank link can include a yoke with a pair of arms extending towards and coupled to the artificial foot. The voice coil valve and the hydraulic actuator can be at least partially disposed between the pair of arms of the yoke.

In accordance with another more detailed aspect of the present invention, the voice coil valve can be disposed in and carried by the piston, and movable with the piston inside the hydraulic chamber. In addition, the hydraulic channel can extend through the piston.

In accordance with another more detailed aspect of the present invention, the prosthetic ankle can include foot coupler mount attached to the artificial foot. The shank link can comprise a yoke with a pair of arms extending towards and pivotally coupled to the foot coupler mount at a single-axis pivot. A force sensor, or a torque sensor, or both can be carried by the prosthetic ankle to measure force, torque, or both applied by the user to the prosthetic ankle or artificial foot. A gyroscope, or an accelerometer, or both can be carried by the foot coupler mount or the artificial foot. An angle sensor can be carried by an ankle shaft of the pivot to measure relative angle between the shank link and the artificial foot. A control system can be coupled to the voice coil valve and the sensors. The control system can include a valve controller carried by the hydraulic chamber and disposed between the pair of arms of the yoke, and a main controller disposed on both sides of the yoke.

In accordance with another more detailed aspect of the present invention, the prosthetic ankle can include a foot coupler mount attached to the artificial foot. The shank link can comprise a yoke with a pair of arms extending towards and pivotally coupled to the foot coupler mount at a single-axis pivot. A force sensor, or a torque sensor, or both can be carried by the prosthetic ankle to measure force, torque, or both applied by the user to the prosthetic ankle or artificial foot. A gyroscope, or an accelerometer, or both can be carried by the foot coupler mount or the artificial foot. An angle sensor can be carried by an ankle shaft of the pivot to measure relative angle between the shank link and the artificial foot. A control system can be coupled to the voice coil valve and the sensors. The control system: opens the voice coil valve when the artificial foot is un-weighted to allow the artificial foot to pivot with respect to the shank link to allow for terrain adaptation; and closes the voice coil valve when the artificial foot is weighted to lock the artificial foot with respect to the shank link to allow the artificial foot to function.

In accordance with another more detailed aspect of the present invention, the prosthetic ankle can include at least three different foot covers or shells having different outer sizes and each having a cavity therein. The artificial foot and at least a portion of the shank link and the hydraulic actuator or damper can fit in each cavity of the at least three different foot covers.

In accordance with another more detailed aspect of the present invention, the voice coil valve can include a permanent magnet and a coil movable with respect to the permanent magnet. A spool can be coupled to the coil and movable therewith, and disposed in and circumscribed by both the coil and the magnet.

In accordance with another more detailed aspect of the present invention, the prosthetic ankle can comprise a mechanical ball lock carried by a piston rod of the hydraulic piston, and releasably engagable with the hydraulic chamber, to lock the hydraulic piston and the hydraulic chamber with respect to one another. The mechanical ball lock can comprise a collar rigidly affixed to the hydraulic chamber and an indentation in the interior of the collar. The piston rod can extend through the collar and can have a hollow therein. At least one hole can be in the piston rod, and at least one ball can be movably disposed in the at least one hole of the piston rod. An engagement pin can be movably disposed in the hollow of the piston rod. The engagement pin can have an enlargement to displace the at least one ball partially into the indentation in the interior of the collar when the indentation is aligned with the at least one hole so that the at least one ball is in both the at least one hole and the indentation to lock the piston rod and the collar with respect to one another.

In addition, the invention provides a prosthetic ankle with a pair of prosthetic members, comprising an shank link configured to be coupled to a remnant limb of an amputee and an artificial foot, movably coupled together to allow movement of the pair of prosthetic members with respect to one another. A hydraulic actuator or damper including hydraulic fluid in a hydraulic chamber is coupled to one of the pair of prosthetic members, and a hydraulic piston is movably disposed in the hydraulic chamber and coupled to another of the pair of prosthetic members. A hydraulic flow channel fluidly is coupled between opposite sides of the chamber to allow hydraulic fluid to move between the opposite sides of the chamber as the hydraulic piston moves therein. A control valve is coupled to the hydraulic flow channel to open or close flow of hydraulic fluid through the flow channel, and thus allow or disallow movement of the piston in the chamber, and thus unlock or lock movement of the pair of prosthetic members with respect to one another. A controller is coupled to the control valve and has circuitry configured to control the control valve based on patient preference, a heel height of footwear coupled to the artificial foot, and/or the slope of the terrain.

In accordance with another more detailed aspect of the present invention, the controller circuitry is configured to change a position (ankle position or relative angle between the foot and the shank link) at which resistance is applied by the control valve to the hydraulic fluid.

In accordance with another more detailed aspect of the present invention, the control valve applies a consistent hydraulic resistance.

In accordance with another more detailed aspect of the present invention, the controller circuitry is configured to control the control valve using:

$$x = \frac{(x_{CL} - x_{DFR})}{(\theta_T - \theta_{FF})}(\theta - \theta_{FF}) + x_{DFR},$$

where $x$=a current valve position, $x_{CL}$=a valve position at which a valve orifice of the control valve is completely closed, $x_{DFR}$=a valve position selected by the amputee that produces an amount of initial dorsiflexion resistance, $\theta$=a current ankle position angle, $\theta_T$=an ankle position angle at which the hydraulic ankle will switch to into a locked state, and $\theta_{FF}$=an ankle position angle when the foot of the device is flat on the ground or when the device initiates a hydraulic dorsiflexion state.

In accordance with another more detailed aspect of the present invention, the controller circuitry is configured to control the control valve using:

$$\theta_T = \theta_{HH} + \delta_S + \delta_P,$$

where $\theta_T$=the ankle position angle at which the hydraulic ankle switches to the locked state, $\theta_{HH}$=a default ankle position angle at which a hydraulic ankle switches to the locked state based on a heel height of the current footwear, $\delta_S$=an offset angle from the default locked ankle position based on the slope of the terrain, and $\delta_P$=an offset angle from the default locked ankle position based on user preference.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIGS. 12a-c are perspective, side and front views, respectively, of the prosthetic ankle of FIG. 1 shown in an anatomical envelope defined by a natural leg and/or ankle and foot;

FIG. 17a is a perspective view of another hydraulic actuator or damper, or hydraulic system, of the prosthetic ankle shown in accordance with another embodiment of the present invention;

FIG. 17b is a side view of the hydraulic actuator or damper, or hydraulic system, of FIG. 17a;

FIG. 17c is a cross-sectional side view of the hydraulic actuator or damper, or hydraulic system, of FIG. 17a, taken along like 17c of FIG. 17a, shown in a locked configuration;

FIG. 17d is a cross-sectional side view of the hydraulic actuator or damper, or hydraulic system, of FIG. 17a, taken along like 17c of FIG. 17a, shown in an unlocked configuration;

FIG. 18a is a partial perspective view of another prosthetic ankle in accordance with an embodiment of the present invention, shown with a snap-on bond ring;

FIG. 18b is a partial, exploded, perspective view of the prosthetic ankle of FIG. 18a, shown with the snap-on bond ring;

Figure 1:
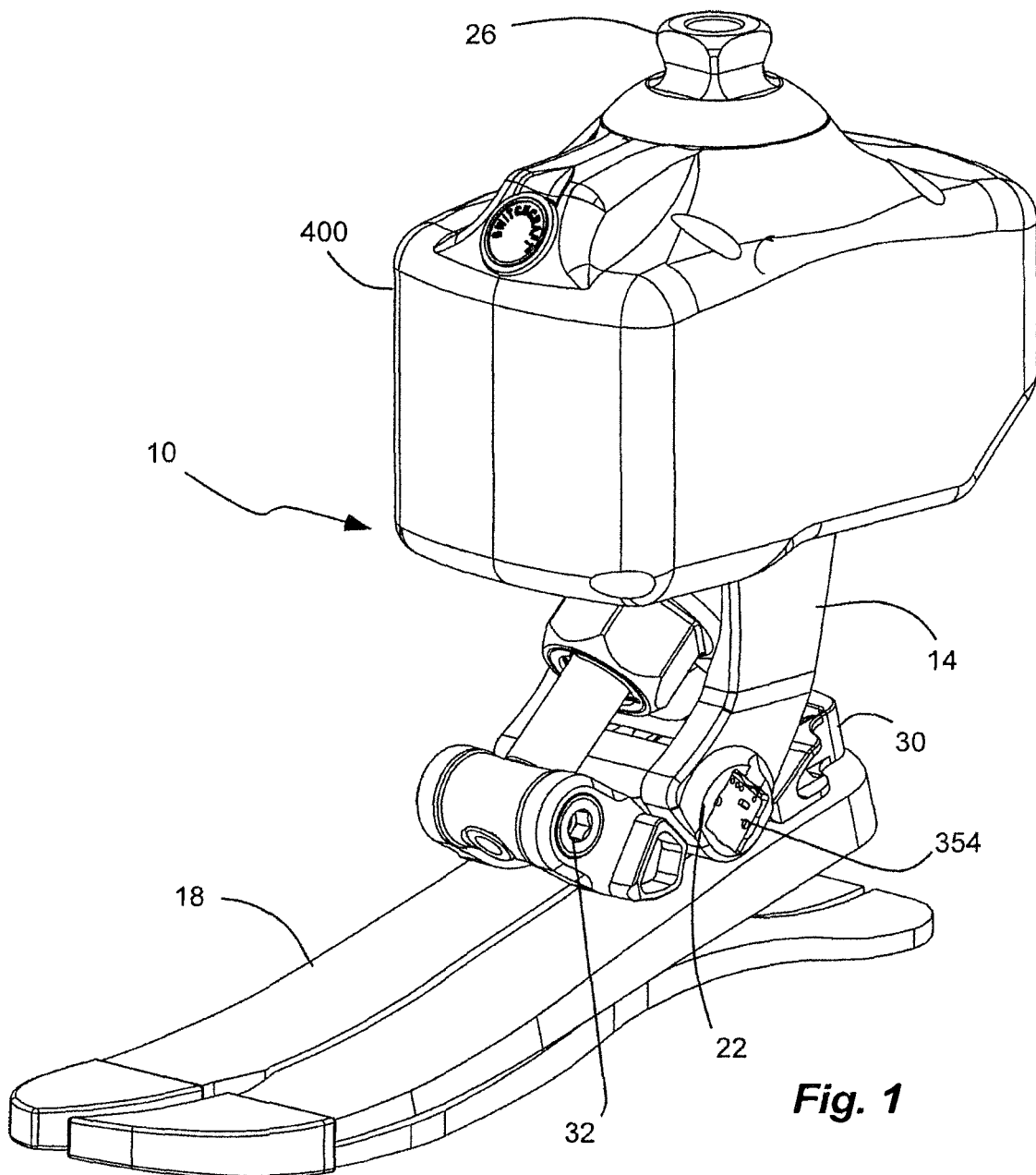
FIG. 1 is a perspective view of a prosthetic ankle in accordance with an embodiment of the present invention, shown with a prosthetic foot attached thereto.
Figure 2:
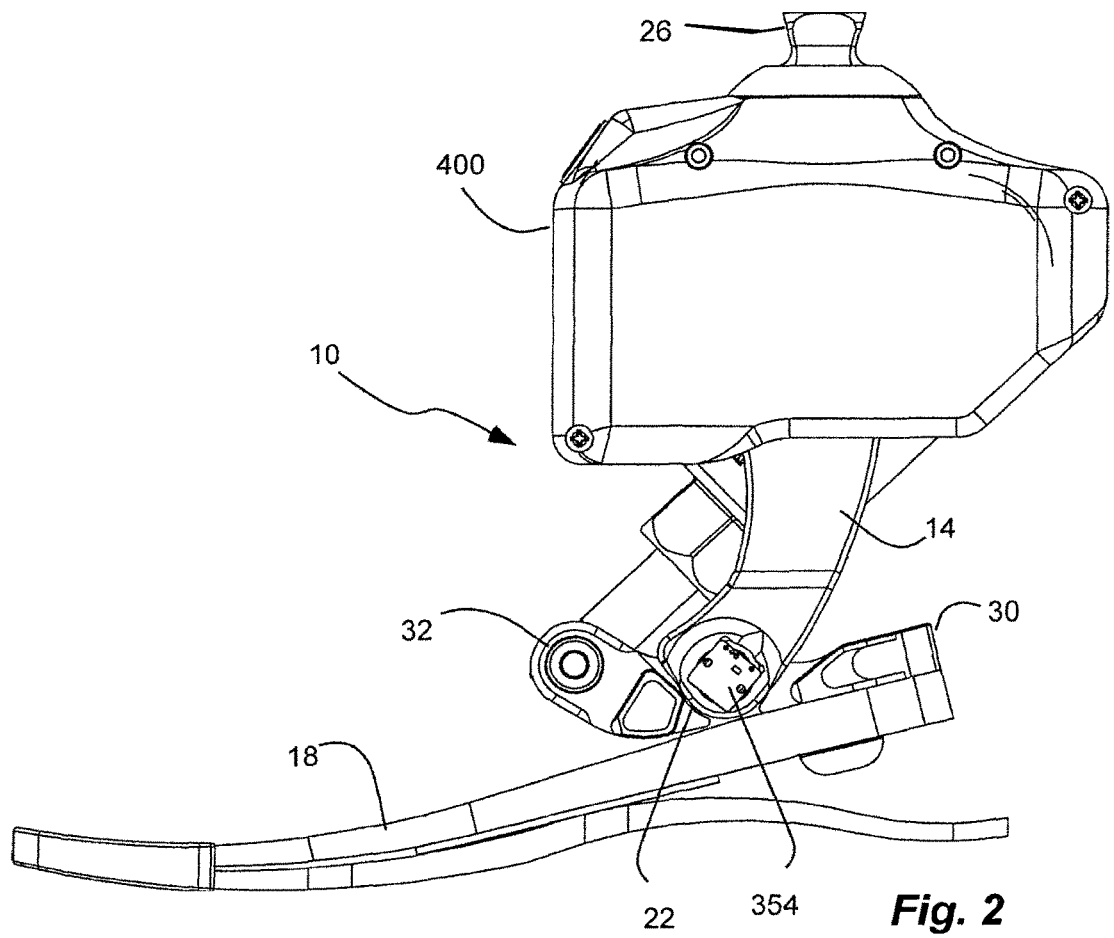
FIG. 2 is a side view of the prosthetic ankle of FIG. 1.
Figure 3:
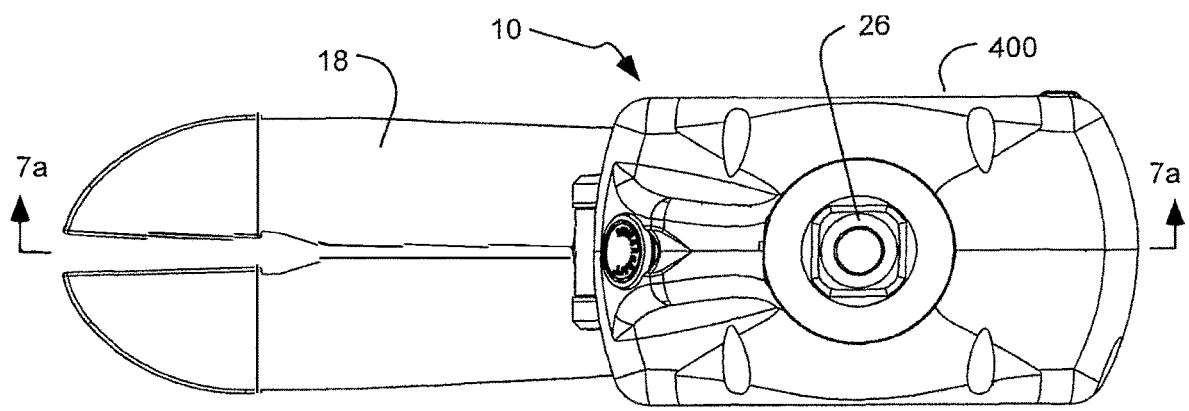
FIG. 3 is a top view of the prosthetic ankle of FIG. 1.
Figure 4:
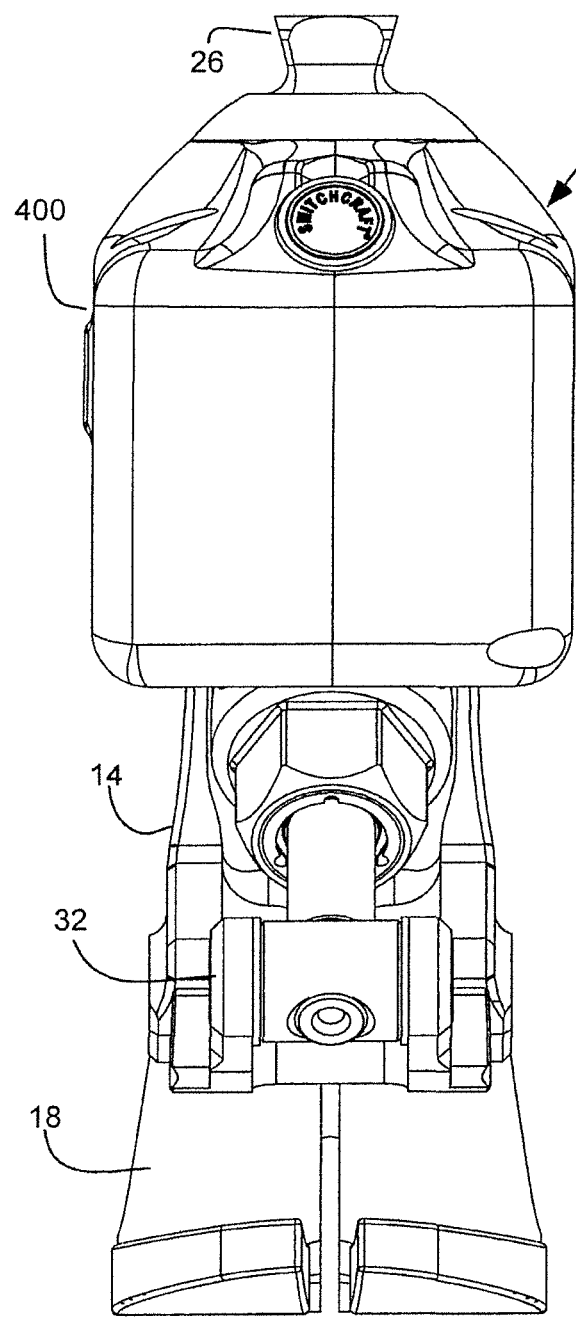
FIG. 4 is a front view of the prosthetic ankle of FIG. 1.
Figure 5:
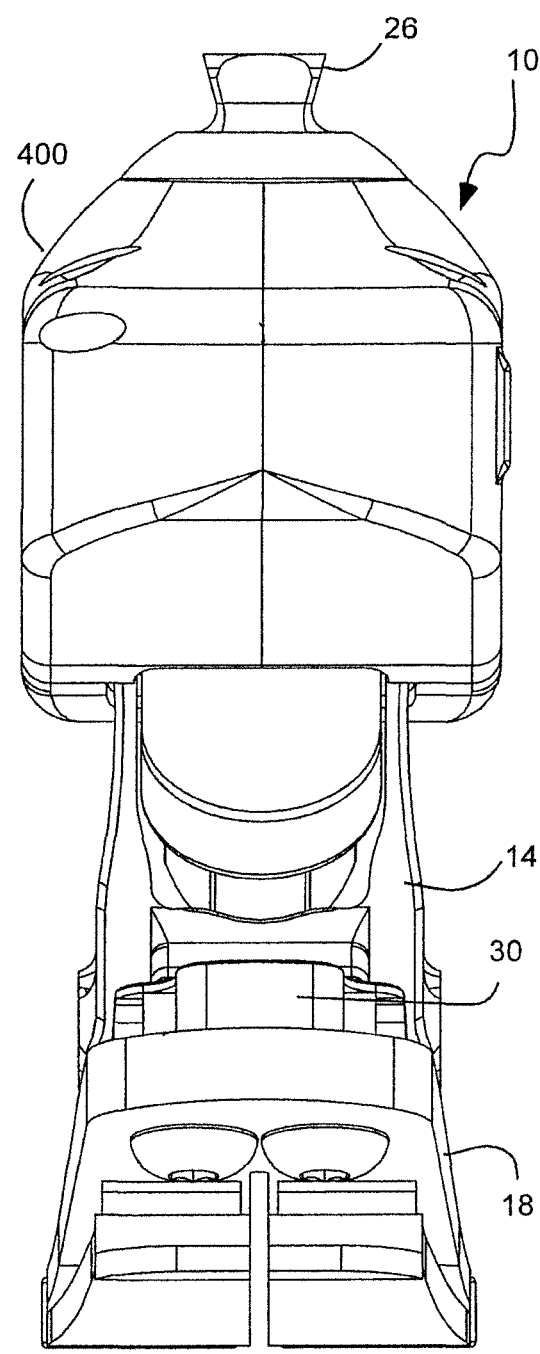
FIG. 5 is a rear view of the prosthetic ankle of FIG. 1.
Figure 6:
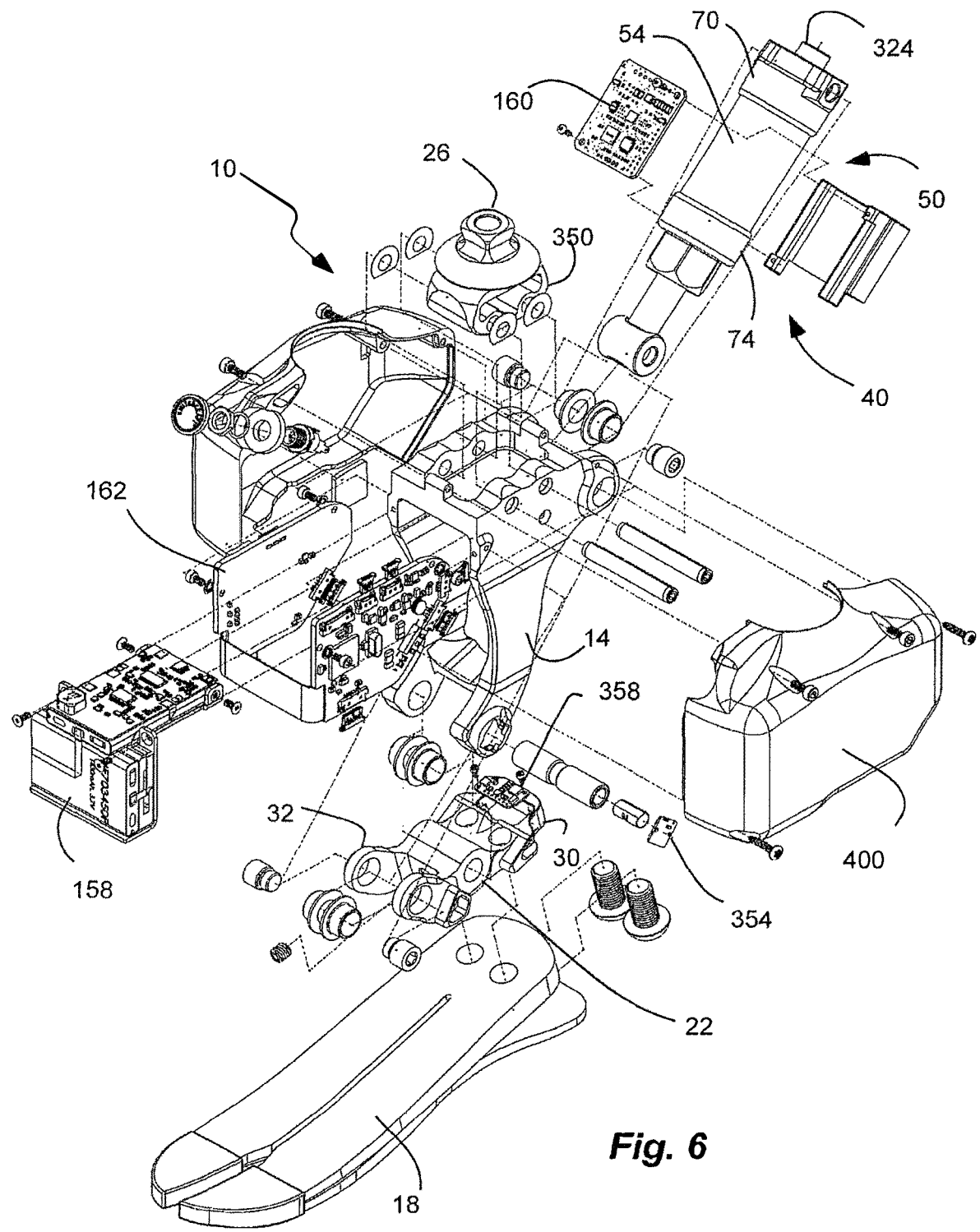
FIG. 6 is an exploded view of the prosthetic ankle of FIG. 1.
Figure 7A:
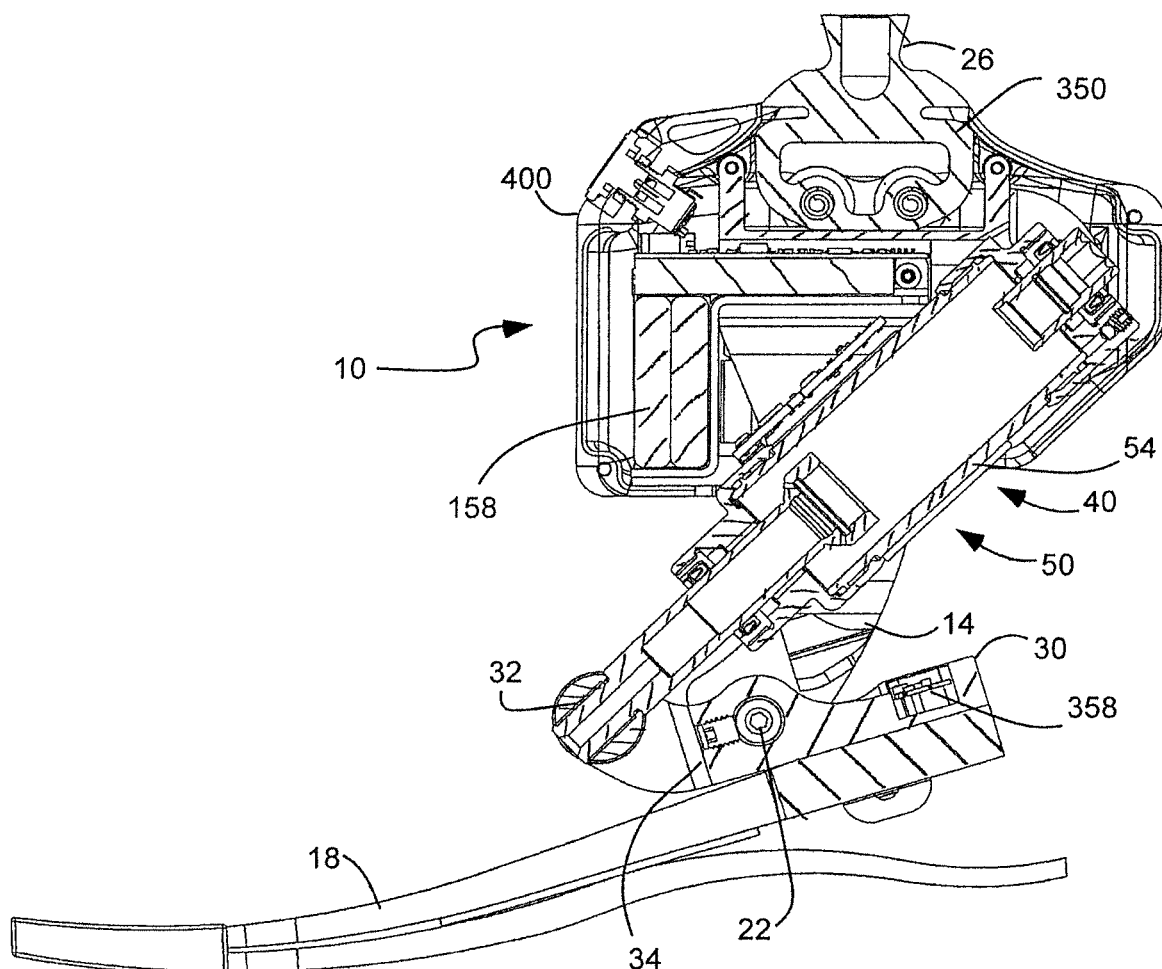
FIG. 7*a* is a cross-sectional side view of the prosthetic ankle of FIG. 1, taken along line 7*a* in FIG. 3 (shown with a control valve removed)
Figure 7B:
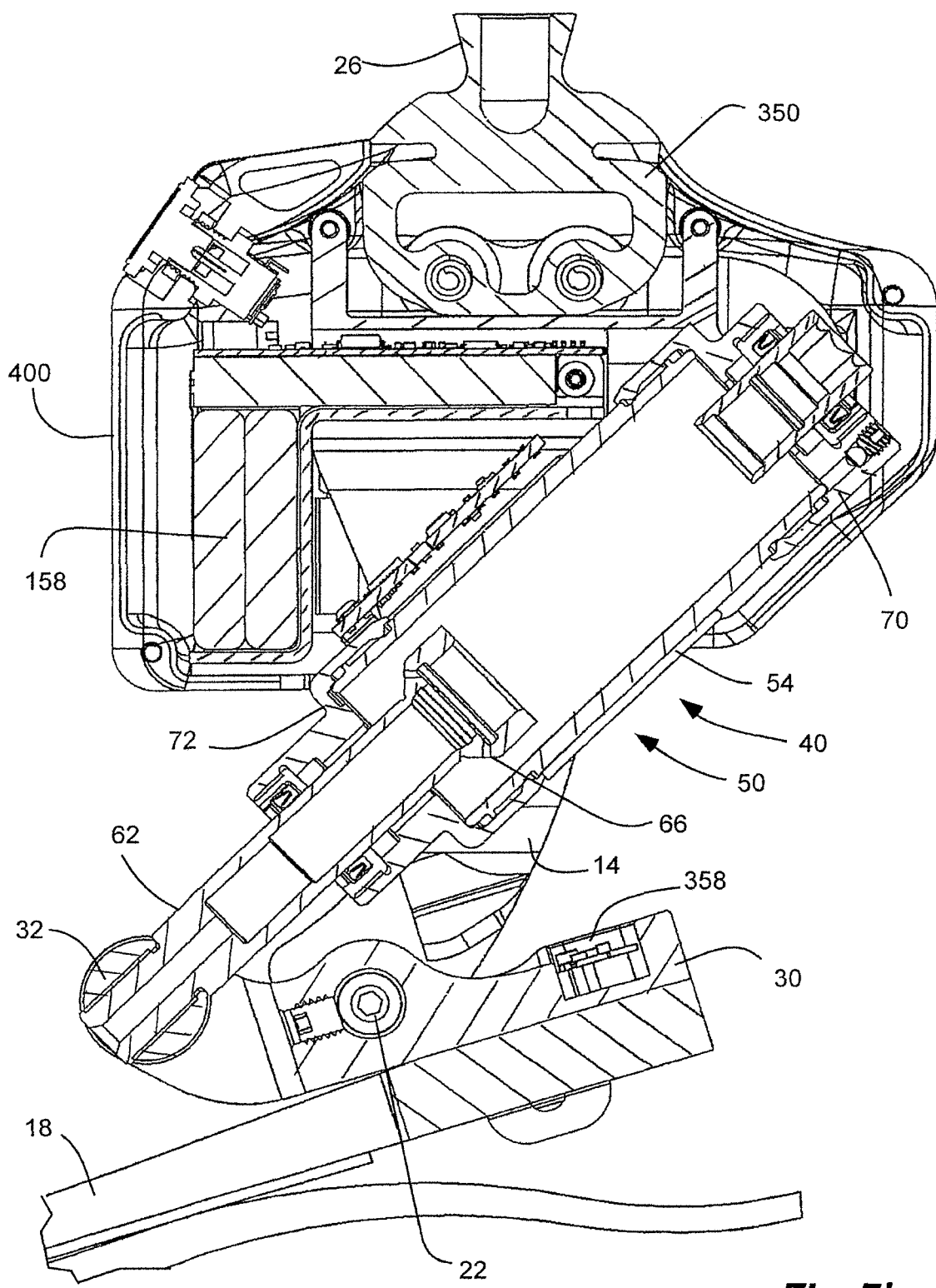
FIG. 7*b* is a detailed cross-sectional side view of the prosthetic ankle of FIG. 1, taken along line 7*a* in FIG. 3 (shown with the control valve removed)
Figure 8:
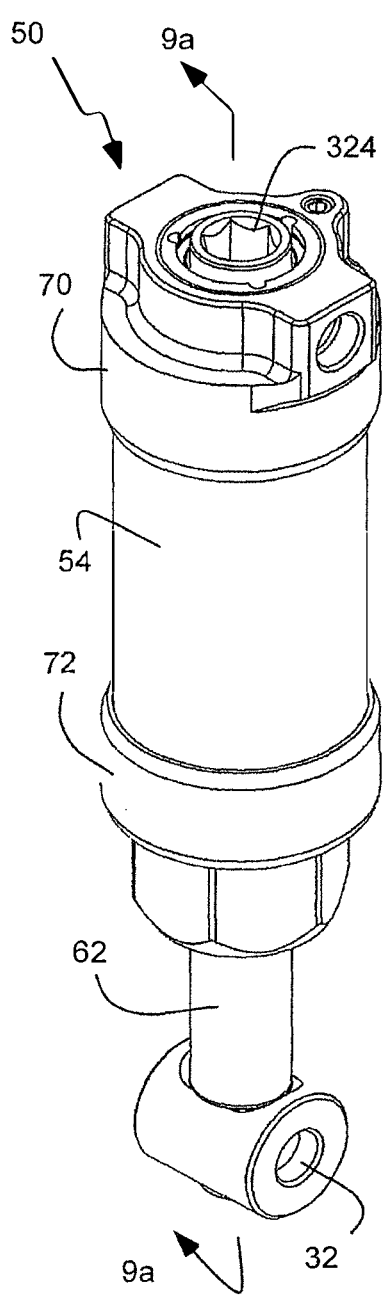
FIG. 8 is a perspective view of a hydraulic actuator or damper, or hydraulic system, of the prosthetic ankle of FIG. 1, in accordance with an embodiment of the present invention.
Figure 9A:
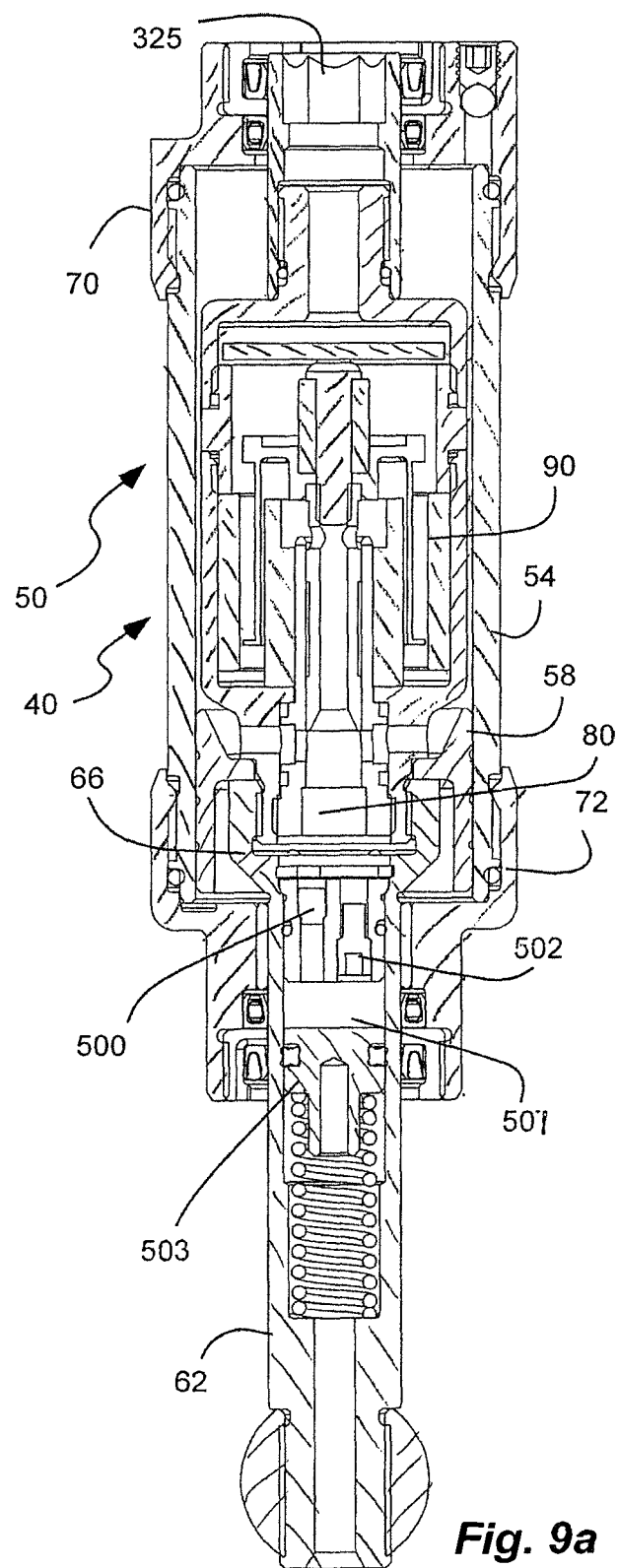
FIG. 9*a* is a cross-sectional side view of the hydraulic actuator or damper, or the hydraulic system, of FIG. 8, taken along line 9*a* of FIG. 8 (shown in an open configuration)
Figures 9B, 9C:
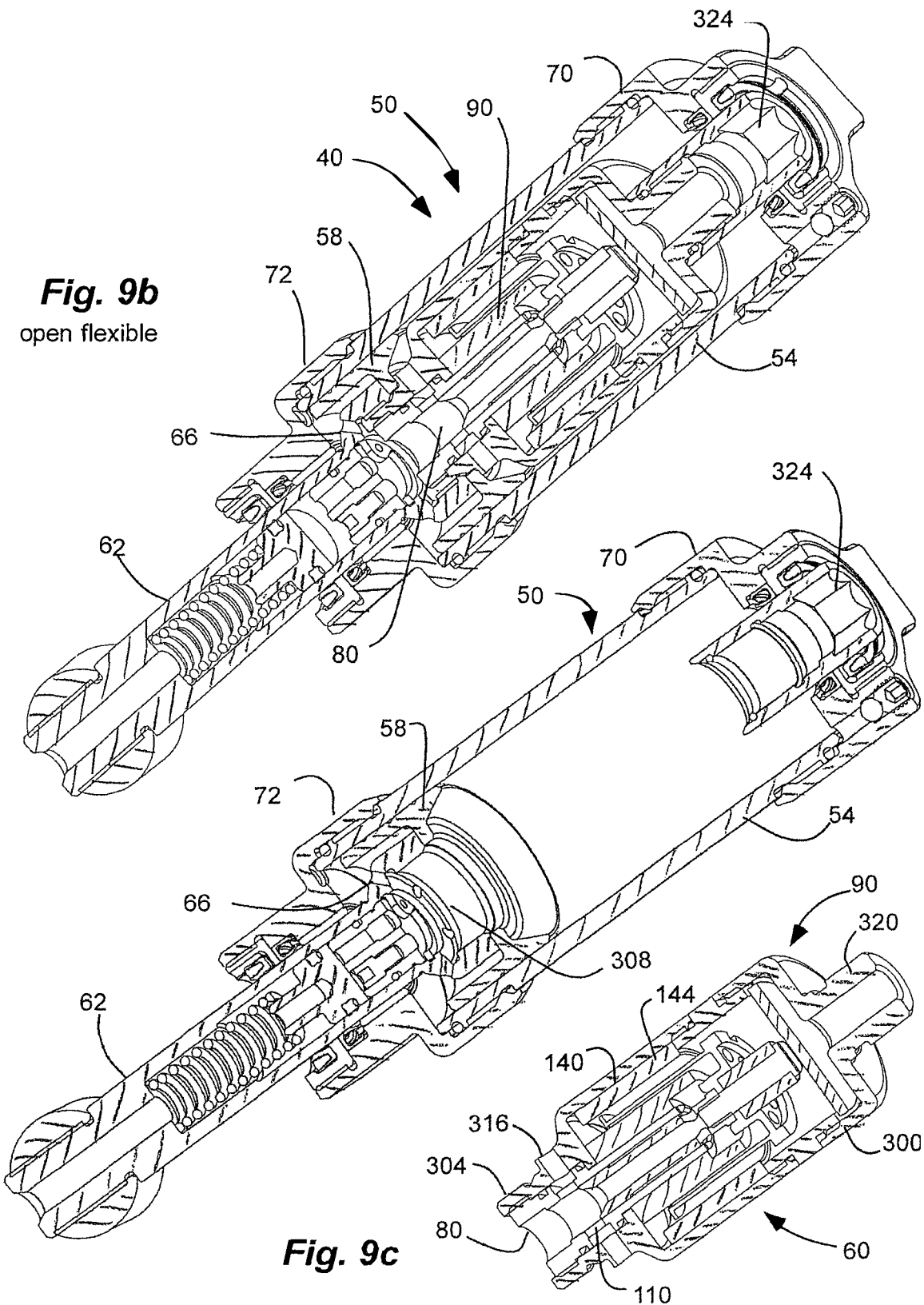
FIG. 9*b* is a cross-sectional perspective view of the hydraulic actuator or damper, or the hydraulic system, of FIG. 8, taken along line 9*a* of FIG. 8 (shown in the open configuration)
FIG. 9c is a cross-sectional partially exploded perspective view of the hydraulic actuator or damper, or the hydraulic system, of FIG. 8, taken along line 9a of FIG. 8 (shown in the open configuration)
Figure 10:
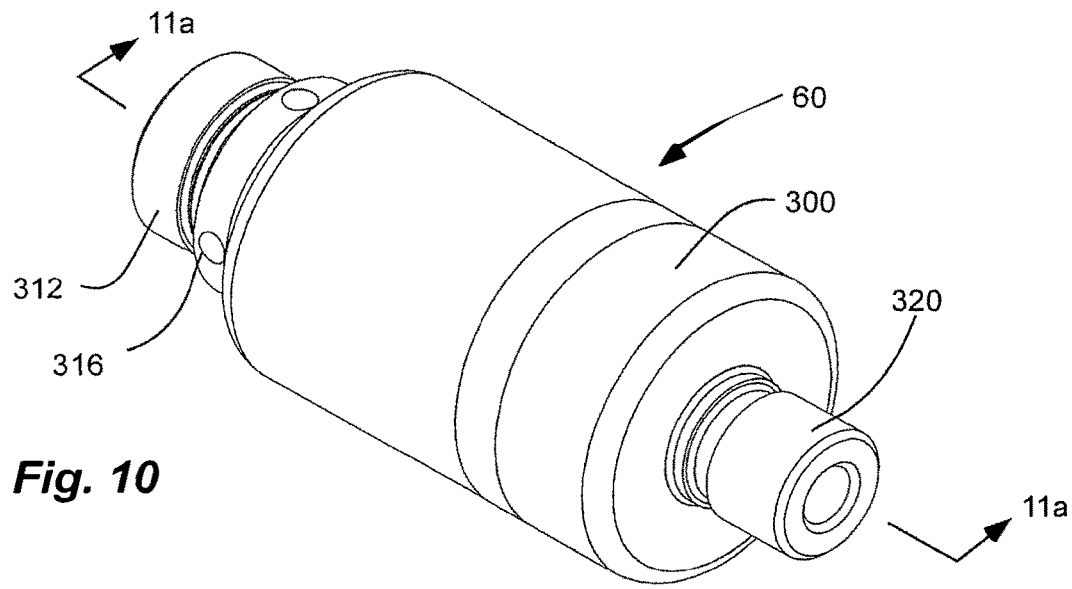
FIG. 10 is a perspective view of the control valve of the prosthetic ankle of FIG. 1.

In the above mentioned figures, hydraulic fluid has been removed for visibility of the components. Although the hydraulic fluid is not shown, those skilled in the art will clearly understand the volumes it occupies, and the channels it flows through.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

The invention provides a prosthetic ankle or joint device for use by an amputee. The prosthetic ankle can have or can be an active dampening ankle joint with limited dorsiflexion-plantarflexion (up and down) pivoting to accommodate footwear of varying heel heights or different environments, such as inclined terrain, by allowing a foot or foot keel or artificial foot to pivot about a horizontal medial-lateral (lateral side-to-side) pivot axis to accommodate the heel height or incline. For example, the foot keel or artificial foot can pivot in plantarflexion (toe pivoting downwardly) for an increase in heel height or when a downward slope is encountered; or the foot keel or artificial foot can pivot in dorsiflexion (toe pivoting upwardly) for a decrease in heel height or when an upward slop is encountered.

The prosthetic ankle device or prosthetic ankle can have an entire system, including control systems, batteries, etc., contained in a housing and in an anatomical envelope defined by a natural leg and/or ankle and foot. In addition, the prosthetic foot can incorporate a valve directly driven by a voice coil or a voice coil valve to control a hydraulic actuator or damper. The voice coil driven valve allows for a valve that is compact, relatively low power, has a fast response time, and has a large dynamic range (that works at both high pressures and low pressures). In addition, the hydraulic system can be mechanically coupled with a flexure-based mechanical system to adjust for side loads. A flexure built into the mounting structure of the hydraulic cylinder can effectively transmit forces to and from the cylinder, while preventing or resisting or minimizing side loads. In addition, the voice coil driven valve can be carried by a piston in a cylinder or chamber of the hydraulic system. In addition, the voice coil driven valve or control valve can be controlled by a controller with an algorithm that changes a position (ankle position or relative angle between the foot and the shank link) at which hydraulic resistance is applied; can vary resistance to flow of hydraulic fluid through the flow channel, and thus movement of the piston in the chamber, and thus influencing a rate of movement of the pair of prosthetic members with respect to one another; and can be a function of a patient's preference, a heel height of current footwear, and/or a slope of the terrain (or combinations thereof). In addition, a mechanically ball lock can lock the hydraulic piston and the hydraulic chamber with respect to one another to lock the prosthetic ankle. In addition, a wireless connection between a user interface and the controller of the prosthetic ankle can allow the patient to move freely while a prosthetist or a clinician makes adjustments; while the user interface can utilize a session that allows the wireless connection to be momentarily interrupted with minimal impact. In addition, the prosthesis or prosthetic ankle or battery thereof can be charged with electromagnetic resonant wireless charging with magnetically coupled and resonantly tuned transmitter and receiver. In addition, an orifice and a check valve can be place in parallel between the hydraulic chamber and a variable volume to allow a spring biased piston in the variable volume to quickly return fluid to the hydraulic chamber through the check valve following a high pressure event to reduce or eliminate long-term "dead band" in the chamber to achieve high pressure in both compression and extension. Furthermore, the prosthetic ankle can fit within multiple different, and standard, foot covers or shells.

The prosthetic ankle can have a pair of prosthetic members that are movably and/or pivotally coupled to one another, and can move and/or pivot with respect to one another, and can be locked with respect to one another and/or have relative movement resisted. For example, the pair of prosthetic members can comprise a shank link coupled to a remnant limb of an amputee, and an artificial foot. The artificial foot can be an energy storing and releasing type foot, such as with leaf springs formed of carbon fibers in a resin matrix. The prosthetic members, or shank link and artificial foot, can pivot with respect to one another to adjust for slope in the terrain and/or accommodate varying heel heights. In addition, the prosthetic member, or shank link and artificial foot, can be selectively locked with respect to one another to preserve the relative position or orientation of the members, or shank link and artificial foot, and to allow the artificial foot to function (such as to store and return energy during the gait cycle). Thus, during the gait cycle, the shank link and the artificial foot can be selectively locked or unlocked. For example, on heel strike (and when substantially un-weighted), the artificial foot can be relatively free to pivot (planter-flexion) with respect to the shank link in order to adjust to the terrain. The ankle or artificial foot can include sensors (e.g. force or load sensor, torque sensor, angle sensor, accelerometer and/or gyroscope) carried by and disposed on the prosthetic ankle and/or artificial foot itself. The movement of the artificial foot with respect to the shank link can provide a comfortable rate of movement as the foot progresses from heel strike to becoming flat on the ground. As the user places weight on the artificial foot and the ankle, a predetermined force or weight threshold is passed triggering one or more weighted states or sub-states thereof, such as initial ground search state, mid-stance state, foot flat state, etc. During the weighted states, the artificial foot can be locked or progressively locked or resisted with respect to the shank link. For example, at mid-stance or foot flat state, the ankle can be locked or progressively locked.

As stated above, the artificial foot can be a leaf spring or energy storing type artificial foot comprising one or more leaf springs or energy storing members that are flexible to bend or flex under loading, and resilient to store and return the energy of the bent or flexed springs or members. For example, such leaf springs can be formed of carbon fiber in a resin matrix. The artificial foot can include a forefoot keel coupled to the shank link, and a footplate coupled to the forefoot keel. The forefoot keel can extend from the shank link at an ankle location of a natural foot, through an arch and/or ball to a toe at a toe location of a natural foot. The footplate can be coupled at the toe of the forefoot keel and can extend to a heel at a heel location of a natural foot. The forefoot keel and the footplate can be split wholly or partially.

The pair of prosthetic members, or shank link and artificial foot, can move in dorsiflexion (toe up or towards shin) and plantarflexion (toe down or away from shin). The prosthetic members can move and/or pivot about a single pivot joint or axle.

A hydraulic actuator or damper can also be coupled to and between the pair of prosthetic members, or shank link and artificial foot, to control or limit the movement and/or pivoting between the members. The terms "hydraulic actuator", "hydraulic damper" and "hydraulic actuator or damper" are used interchangeably herein to refer to a hydraulic system that imposes some type of limitation or control on the movement of a hydraulic fluid, and thus some type of limitation or control on the relative movement between the prosthetic members. The hydraulic system can be a hydraulic damper that simply limits or resists movement of the hydraulic fluid, and thus simply limits or resists movement between the pair of prosthetic members. The hydraulic system can be a hydraulic actuator that includes a hydraulic motor that drives or creates hydraulic pressure to drive movement between the pair of prosthetic members. Such a hydraulic actuator can also be operated as a damper.

The hydraulic system can include a hydraulic separator, such as a piston or vane, movable in a hydraulic chamber, such as a linear cylinder or rotary chamber, to displace hydraulic fluid from one side of the working chamber to the other. The piston can be coupled to one of the prosthetic members (e.g. the artificial foot), while the chamber is coupled to the other of the prosthetic members (e.g. the shank link) in the embodiment of a linear piston damper. Such couplings can be secondary pivotal couplings, separate from a primary pivot between the pair of members. The piston can divide the chamber into opposite sides and the hydraulic system can be configured to displace the fluid from one side of the piston to the other, or from one side of the chamber to the other. Thus, the hydraulic system can have a hydraulic flow channel fluidly coupled between the opposite sides of the chamber to allow the hydraulic fluid to move between the opposite sides of the chamber as the piston moves therein. In one aspect, the hydraulic system can include an overflow reservoir to accommodate the different volumes of the opposite sides of the chamber due to the volume of piston rod coupled to the piston. In another aspect, the hydraulic system can include a piston rod on both sides of the piston, which exits the working chamber on both sides, commonly termed a "thru-rod" damper, so that the sum of the volume on both sides of the chamber during the stroke remains constant.

A control valve can be coupled to the hydraulic flow channel to vary resistance to the hydraulic fluid flow or vary the flow rate. Prior art solenoid valves have been used to vary flow. Solenoid valves typically have a stationary iron core with a coil, and a movable iron armature that is moved when current is applied to the coil. Solenoid valves also typically rely on a spring for return movement when the current is removed from the coil. Thus, solenoid valves often have an on-off operation. Solenoid valves generate force proportional to the square of the current (and are thus non-linear). Solenoids are relatively inexpensive. It has been recognized by the inventors, however, that solenoid valves are or can be limited by unidirectionally driven movement in that the armature only moves in one direction regardless of the polarity of the current applied, and that a spring is required for return movement. In addition, it has been recognized by the inventors that solenoid valves are or can be limited by requiring additional current to overcome the spring force of the spring, thus requiring greater power consumption. In addition, it has been recognized by the inventors that solenoid valves are or can be limited by slower response times and/or non-linear response time (and force).

The inventors have recognized that the control valve can include an electric actuator, coupled to a hydraulic valve, to reciprocally and selectively position the valve, or spool thereof, in a bidirectional movement based on the polarity of the current applied to the actuator. Thus, the valve can be bi-directionally driven in back and forth directions, and bi-directionally positioned. The electric actuator includes a permanent magnet and a coil movable with respect to one another. The permanent magnet can have a magnetic field in which the coil moves when a current is applied to the coil. As well, the same response can be generated when the magnet moves, and the coil remains stationary, when electricity is used. The amount of current can be selected and varied to selectively position the coil with respect to the magnet. The polarity of the current can be selected and changed to select and change the direction of travel of the coil with respect to the magnet. The force produced by the actuator is proportional (and substantially linear) to the current applied (and the velocity of the coil is proportional to the voltage applied), unlike a solenoid (with non-linear time and force response). Thus, the actuator has a substantially linear time and force response. The movement and force of the voice coil motor is based on the Lorentz Force principle and equation, unlike a solenoid. In addition, the direction of movement of the coil can be selected, driven and varied by selecting and varying the polarity of the current, unlike a solenoid (which has the same direction of travel irrespective of polarity; i.e. changing the polarity of a solenoid does not alter the direction). Thus, the direction of travel of the coil is based on the polarity of the current. The actuator, and thus the valve, has a rapid response rate (i.e. greater than 100 cycles per second), and a low power consumption (i.e. less than 1.8 Watts, or 150 mAmps @ 12V), unlike a solenoid. Such an actuator or valve can be referred to as a voice coil or voice coil valve. The actuator is coupled to the hydraulic valve, which is operatively coupled in the hydraulic flow path. The valve includes an orifice and a spool movable with respect to one another. The actuator is coupled to the valve to move the orifice and the spool with respect to one another to selectively resist flow of the hydraulic fluid through the orifice. In one aspect, the actuator can move the spool with respect to the orifice. Thus, the hydraulic valve selectively varies the resistance of the hydraulic valve to the flow of hydraulic fluid through the flow channel.

The control valve and electrical actuator thereof can be operatively coupled, or electrically coupled or wirelessly coupled, to control electronics, such as a circuit board with a microprocessor, forming a computer to control the control valve, and thus the hydraulic system or hydraulic actuator or damper. The computer or control electronics can utilize a control algorithm. The computer or control electronics can vary resistance to flow of hydraulic fluid through the flow channel, and thus movement of the piston in the chamber, and thus influencing a rate of movement of the pair of prosthetic members with respect to one another. In addition, the computer or control electronics can open or open or close the valve (or flow of hydraulic fluid through the flow channel thereof), and thus allow or disallow movement of the piston in the chamber, and thus unlock or lock movement of the pair of prosthetic members with respect to one another. The computer or control electronics can control the hydraulic valve to vary the flow rate of the hydraulic fluid, and thus the resistance to bending, of the ankle. The computer can vary the compression and extension of the hydraulic system or hydraulic actuator or damper during the gait cycle of a prosthetic ankle; and thus control the dorsiflexion and plantarflexion of the prosthetic ankle during gait. The computer and the control valve can vary the resistance and the flow rate of the compression and/or extension of the hydraulic system during both dorsiflexion and plantarflexion of the prosthetic ankle or members thereof. The computer or control electronics can change the position (ankle position or relative angle between the foot and the shank link) at which hydraulic system applies resistance. The computer or control electronics can change the position based on the patient's preference, a heel height of the current footwear, and the slope of the terrain. The control algorithm can smoothly transition between ankle motion due to both 1) pivoting of the foot about the pivot and deflection of the artificial foot, and 2) motion only from foot deflection.

As stated above, the prosthetic ankle can include sensors, such as force or load sensor, torque sensor, angle sensor, accelerometer and/or gyroscope. These sensors can be carried by and disposed on the prosthetic ankle and/or artificial foot itself. For example, a force or load sensor, a torque sensor, or both, can be disposed on or carried by the shank link or a connector thereof to measure force, torque, or both applied by the user to the prosthetic ankle or artificial foot. As another example, an angle sensor can be carried by an ankle shaft of the pivot between the shank link and the artificial foot to measure relative angle between the shank link and the artificial foot. As another example, an accelerometer, a gyroscope, or both can be carried by a foot coupler mount or the artificial foot to sense or measure impact, orientation, etc. Disposing the sensors on the prosthetic ankle and/or artificial foot allows the prosthetic ankle to be a unitary device without components disposed on other structure, such as pylons. Similarly, locating an angle sensor between the shank link and the artificial foot allows relative orientation to be determined without having to determine a relative orientation of other structure, such as a pylon, and without having to locate sensors on a pylon.

As illustrated in FIGS. 1-16, a prosthetic ankle or joint, indicated generally at 10, is shown in an example implementation in accordance with an embodiment of the invention. The prosthetic ankle 10 includes a pair of prosthetic members, namely an upper member or shank link 14, and a lower member or artificial foot 18, that are pivotally coupled together at a primary pivot and/or single-axis pivot and/or ankle shaft 22. The primary pivot 22 can include an axle and bearings. The shank link 14 can be disposed at a location of a natural ankle, while the artificial foot 18 can be disposed at a location of a natural foot. The shank link 14 can have a connector 26 at distal end or top thereof, such as pyramid connectors as known in the art, for attachment to a socket. The force and torque sensor can be an integral part of the connector 26. Various aspects of robust and compact force and torque sensor are found in U.S. patent application Ser. No. 13/015,423, filed Jan. 27, 2011, which is hereby incorporated herein by reference. It is desirable in prosthetic control systems to measure both the vertical force applied to the product and the torque applied in the sagittal plane. Because the torque generates strains that are much greater than those generated by the force, it is difficult to design a single sensor that measures both of these signals. The socket can be attached to a remnant limb of the amputee. Such sockets and connectors are known in the art. In use, the lower member or artificial foot can move with respect to the upper member or shank link in dorsiflexion (toe up or towards shin) and plantarflexion (toe down or away from shin). The upper prosthetic member can comprise the shank link and the connector.

The shank link 14 can comprise a yoke with a pair of arms extending towards and coupled to the artificial foot 18. The distal ends of the pair of arms can be coupled to the artificial foot. The connector 26 can be affixed to a top of the yoke. A space or gap can be defined between the pair of arms.

The lower member of the pair of prosthetic members can comprise the artificial foot 18 and a coupler or mount. A flexure can be built into the mounting structure of a hydraulic cylinder. The flexure can have a high stiffness (or a relatively higher or greater stiffness with respect to a lower stiffness) in a direction parallel to the line of action of the hydraulic cylinder or chamber to effectively transmit forces to and from the cylinder or chamber, but can also have a low stiffness (or a relatively lower or lesser stiffness with respect to the higher or greater stiffness) in at least one direction perpendicular to the line-of-action to prevent or resist side loads from being transmitted to the cylinder or chamber. The coupler or mount can be a flexure based foot coupler mount 30 attached or mounted directly to the artificial foot 18, and coupled between the artificial foot and the shank link 14 (and the hydraulic actuator or damper). The single-axis pivot and/or the ankle shaft 22 can be formed in or disposed in the foot coupler mount 30, and the shank link and the artificial foot can pivot with respect to one another about the ankle shaft in the foot coupler mount. In addition, a hydraulic pivot 32 can be formed in or disposed in the foot coupler mount 30 (and the hydraulic chamber or piston pivots with respect to the artificial foot about the hydraulic pivot). A flexure 34 can be formed in or disposed in the foot coupler mount 30 between the pivots 22 and 32, and can be capable of flexing in a direction perpendicular to the line-of-action of the hydraulic cylinder as a result of an applied force or torque. The flexure 34 can be formed by a reduced cross-sectional area between and with respect to the cross-sectional area of the foot coupler mount 30. The flexure 34 can act as a flexure bearing, and can isolate the hydraulic cylinder from side loading in the system when a force or torque is applied. Thus, the flexure based foot coupler mount can be capable of preventing excessive seal wear and/or binding in the hydraulic cylinder. Side loads are common in prosthetic devices, and can, at a minimum, cause premature failure of hydraulic cylinder seals and, at the worst, can cause binding or bending of the cylinder components, especially the shaft. In one aspect, ball joints can be utilized at both ends of the cylinder to resist transmittal of side loads by movement of the ball joints, but such ball joints can greatly increases the eye-to-eye length of the cylinder, which may not fit within the anatomical envelope of a natural leg. In another aspect, the cylinder can be mounted on trunnions, but the trunnions can transmit side loads. The flexure system can be used with trunnions to minimize side loads, while at the same time allowing the cylinder to fit within the anatomical envelope of the natural leg (as shown in FIGS. 12*a-c*). In another aspect, the flexure can be built into the shaft.

The prosthetic ankle 10 also has a hydraulic system 40 that can include a hydraulic actuator or damper 50 and a control valve 60. The hydraulic system 40 is coupled between the upper and lower members, or shank link and prosthetic foot 14 and 18. The hydraulic actuator or damper 50 includes a hydraulic chamber, namely a cylinder 54, pivotally coupled to the upper member or shank link 14, and a piston 58 with a piston rod 62 pivotally coupled to the lower member or artificial foot 14. The pivotal connections between the hydraulic actuator or damper and the upper and lower members form secondary pivots, separated from the primary pivot or ankle shaft. In another aspect, the coupling of the hydraulic actuator or damper can be reversed, with the cylinder coupled to the lower member or artificial foot, and the piston rod coupled to the upper member or shank link. The piston 58 can be cylindrical and can slidably move within the cylinder 54. In addition, the piston 58 divides the cylinder 54 or chamber into opposite sides. The cylinder 54 can be formed by a cylinder disposed between opposite caps 70 and 72, one of which is an upper cap 70 that is pivotally coupled to the upper member or shank link 14 (with an axle and bearings), and the other of which is a lower cap 72 that has an aperture to slidably receive the piston rod 62. The piston rod 62 is pivotally coupled to the lower member or artificial foot 18 or foot coupler mount 30 (with an axle and bearings).

In addition, the linear piston damper system (or piston 58 and cylinder 54) can utilize tightly toleranced components which eliminate the need for elastomeric seals to separate the sides of the hydraulic chamber. By using a "metal-on-metal" fit between the piston and cylinder, the seal drag (or stiction) which would be transferred to the amputee as a jarring or disjointed feeling, can be entirely removed from the system, or greatly reduced. This also provides for greater reliability and longevity of the system because there is no elastomeric seal to be damaged or wear out. The precision that can be required to form a hydraulic working chamber capable of locking without weeping can require a gap between the acting surfaces of the piston and cylinder on the order of 0.005 mm (0.00021 n). Furthermore, the surface finish that can be required to facilitate smooth actuation on both surfaces of the piston and cylinder can be between 0.20 to 0.41 μm (8 to 16 μin) Ra finish.

Hydraulic fluid (not shown for clarity of the components) can fill the cylinder 54 or chamber, and can be displaced from one side of the cylinder 54 or chamber (or piston 58) to the other as the piston 58 moves therein. A hydraulic flow channel 66 is fluidly coupled between the opposite sides of the cylinder 54 or chamber (or piston 58) to allow the hydraulic fluid to move or displace between the opposite sides of the cylinder 54 or chamber (or piston 58) as the piston 58 moves therein. The control valve 60 can be carried by the piston 58, and movably disposed within the cylinder 54. Thus, the hydraulic flow channel 66 can extend through the piston 58.

As indicated above, the prosthetic ankle 10 and the hydraulic system 40 include a control valve 60 coupled to the hydraulic flow channel 66 to open and close, and/or vary resistance to, flow of hydraulic fluid through the flow channel 66, and thus movement of the piston 58 in the chamber 54, and thus unlock or lock, and/or influence a rate of movement of, the pair of prosthetic members 14 and 18 with respect to one another. As discussed above, the control valve 60 includes a hydraulic valve 80 that directly contacts and acts upon the hydraulic fluid, and an actuator 90 that drives and controls the hydraulic valve 80. The hydraulic valve 80 and the actuator 90 can be fixed together as a single, operable unit, i.e. the control valve 60, that can be coupled to and carried by the hydraulic system 40, and the hydraulic actuator or damper 50, such as by the piston 58. Thus, the control valve 60 can be removed and replaced as a single unit to facilitate repair or custom applications.

The hydraulic valve 80 of the control valve 60 is operatively coupled in the hydraulic flow path or channel 66, and includes at least one orifice 110 and a spool 114 movable with respect to one another to selectively resist flow of the hydraulic fluid through the orifice. The spool 114 can be selectively positioned with respect to the orifice(s) 110 to selectively close and open the orifice, and/or increase and decrease a cross-sectional area through which the hydraulic fluid can flow. The spool 114 can have a center hole 116 therethrough and cross holes 116*a* formed laterally through the spool, and can be pressure balanced through the center hole 116 and the cross holes 116*a*. The spool 114 can have a distal end 118 (or at least one distal opening) that is selectively positionable with respect to the orifice 110. The orifice(s) 110 can be formed in a sleeve 122 circumscribing the spool 114. The spool 114 can slide within the sleeve 122. Thus, the spool 114 can be selectively positioned by the actuator to selectively position the spool 114 or end 118 thereof with respect to the orifice 110, and close or open the orifice, and/or selectively increase and decrease a cross-sectional area through which the hydraulic fluid can flow. An outer diameter of the spool 114 can match an inner diameter of the sleeve 122 with a tight tolerance so that the spool and sleeve seal with respect to one another. In another aspect, the sleeve can be coupled to the actuator and move relative to the spool and/or the orifice could be formed in the spool. In another aspect, the spool can have a distal opening formed laterally through the spool that can be selectively positioned with respect to the orifice 110.

As stated above, the electric actuator 90 is coupled to the hydraulic valve 80 to move the spool 114 with respect to the orifice(s) 110. The actuator 90 includes a permanent magnet 140 and a coil 144 movable with respect to one another. The magnet 140 is part of a magnetic circuit that includes a housing 140a and a pole piece 140b both of which are made from a magnetically conductive material such as low carbon steel. Both the housing 140a and the pole piece 140b can be annular, with the housing circumscribing the pole piece and forming an annular gap therebetween. The magnet 140 has or creates a magnetic field that induces magnetic flux across an air gap between an inside diameter of the magnet 140 or housing 140a and an outside diameter of the pole piece 140b. The coil 144 can have an annular wall or cup sized to fit in the air gap between the magnet 140 or housing 140a and the pole piece 140b. The coil 144 can include wires wrapped or coiled around the wall or cup. Thus, the coil 144 can be movably positioned in the magnetic field of the magnet 140. A current can be applied to the coil 144 to move the coil with respect to the magnet 140. As described above, the current applied to the coil 144 in the magnetic field of the magnet 140 produces a force that is directly proportional to the electric current applied. In addition, the coil 144, and thus the control valve 60, has a substantially linear time and force response. Furthermore, the coil 144, and thus the spool 114, is bi-directionally driven by the current, or polarity thereof. The electric current applied to the coil 144 causes the coil, and thus the spool 114, to move in either a first direction or a second direction based on a polarity of the electric current. Thus, the coil 144 and spool 114 are reciprocally positioned by selectively changing the polarity of the electric current applied to the electric actuator 90 or coil 144 thereof. Thus, the spool 114 can be selectively positioned and bi-directionally driven in back and forth directions, so that the hydraulic valve 80 selectively varies the resistance, or effective flow area or size of the orifice(s) 110, of the hydraulic valve 80, via the position of the spool 114 with respect to the sleeve 122, to the flow of hydraulic fluid through the flow channel or orifice(s) 110. The control valve 60 or actuator 90 can have a rapid response rate, greater than 100 cycles per second, and a low power consumption, less than 1.8 Watts (i.e. or 150 mA @ 12V). Furthermore, the control valve 60, and the coil 144 thereof, can be selectively and proportionally positioned, proportional to an amount of the electric current applied to coil or the control valve. Thus, a selective and variable amount of electric current with variable polarity applied to the coil or control valve selectively and proportionally varies the resistance of the control valve, or the hydraulic valve 80 thereof, to the flow of hydraulic fluid through the flow channel. While the coil has been described above as movable with respect to a permanent magnet, it is contemplated that such a configuration can be reversed, with the magnet coupled to the spool or sliding tube, and movable with respect to the coil.

The control valve 60 can be characterized as a voice coil actuated valve or voice coil valve, and the actuator 90 can be characterized as a voice coil. Therefore, the prosthetic ankle 10 and hydraulic system 40 thereof can utilize a voice coil actuated valve. As noted above, the control valve 60 or voice coil valve described above provides bi-directional positioning, proportional control, rapid response and/or low power consumption. The use of the control valve 60 or voice coil valve described above allows the coil and spool to be driven in either direction without requiring a spring for return motion, which in turn reduces the power consumption of the control valve, which can result in longer operational periods between charging and/or smaller power supplies (e.g. batteries), resulting in greater freedom and less weight for the amputee. In addition, the use of the control valve 60 or voice coil valve described above allows the hydraulic system 40 and prosthetic ankle 10 to have a faster response time to provide a more natural gait to the amputee and/or to provide a more natural transition. The voice coil valve provides a fast response time (<20 ms), a large pressure range (up to about 3000 psi), a fully proportional control (can go to any position as opposed to only open or closed), and a low power (about 200 mW to hold a static position). Thus, the voice coil valve allows the hydraulic ankle to have smooth motion that can adapt on-the-fly to changes in terrain and footwear.

The control valve 60 or voice coil valve can be oriented with a path of travel of the coil 144 and spool 114 parallel with a path of travel of the piston 58. The voice coil valve can be disposed in and carried by the piston, and movable with the piston inside the hydraulic chamber. The hydraulic channel can extend through the piston. In addition, the voice coil valve and the hydraulic actuator can be at least partially disposed in the space or gap between the pair of arms of the yoke. The position and orientation of the control valve 60 or voice coil valve can create a more compact and smaller profile for the prosthetic ankle, and thus greater freedom, comfort and natural movement for the amputee, because the control valve 60 or voice coil valve can be larger than prior art solenoid valves.

In addition, the spool 114 can be substantially concentric with and/or substantially disposed within the coil 144 (and the magnet 140) to reduce the length of the actuator 90, control valve 60, and hydraulic system; thus, reducing the size of the prosthetic ankle to fit with the anatomical envelope defined by a natural leg and/or ankle and foot.

As described above, one or more orifices 110 in the sleeve 122 can be selectively exposed by the end 118 of the spool 114. The orifice(s) 110 can have a longitudinally varying width with a discrete change in width from a proximal end to a distal end along a longitudinal length of the orifice. For example, the orifice can have a larger or wider proximal end, and a smaller or narrower distal end. In one aspect, the width of the opening can taper from larger to smaller in a continuous transition. In another aspect, the orifice can have two or more discrete widths formed by orifices sharing a common boundary that is open between the orifices. The orifice(s) can have a larger proximal rectilinear (square or rectangular) shape and a smaller distal rectilinear shape, which share a common boundary and that are open to one another. In another aspect, a larger number of orifices(s) and opening(s) can be aligned or misaligned. In another aspect, the shape, size, number and/or location of the orifice(s) and/or opening(s) can be configured to provide the two linear regions.

Figure 11A:
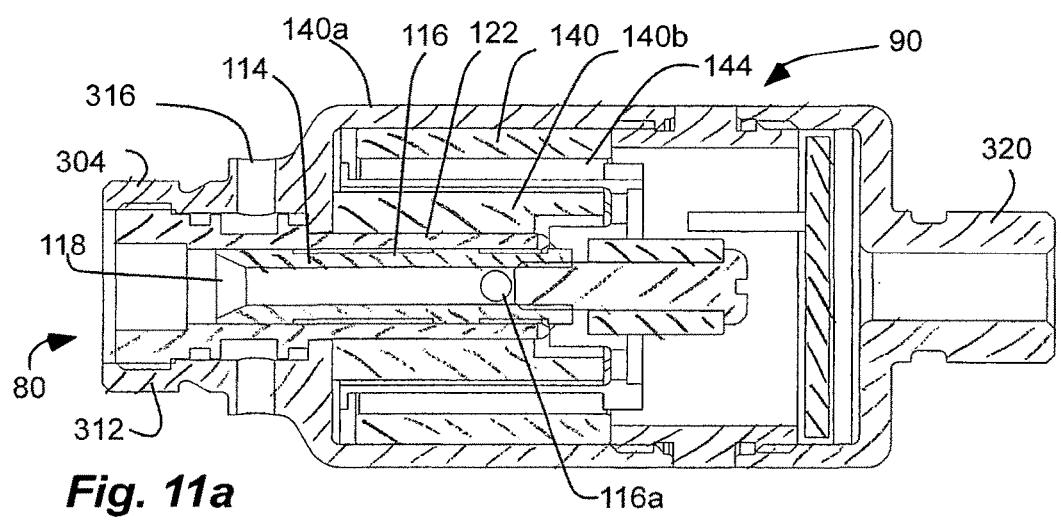
FIG. 11a is a cross-sectional side view of the control valve of FIG. 10, taken along line 11a in FIG. 10, and shown in the closed configuration.
Figure 11B:
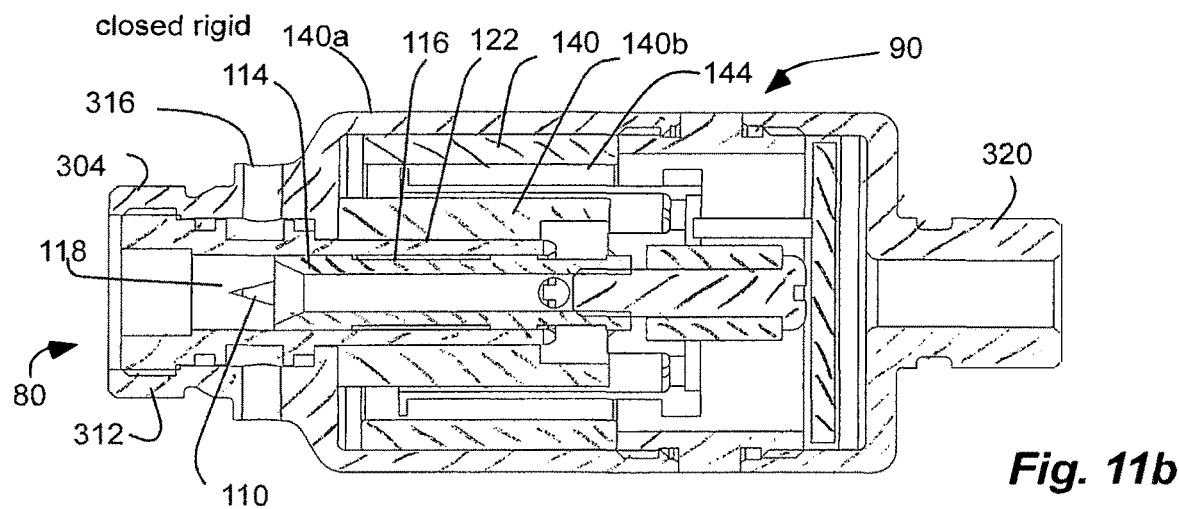
FIG. 11b is a cross-sectional side view of the control valve of FIG. 10, taken along line 11a in FIG. 10, and shown in an open configuration.
Figure 11C:
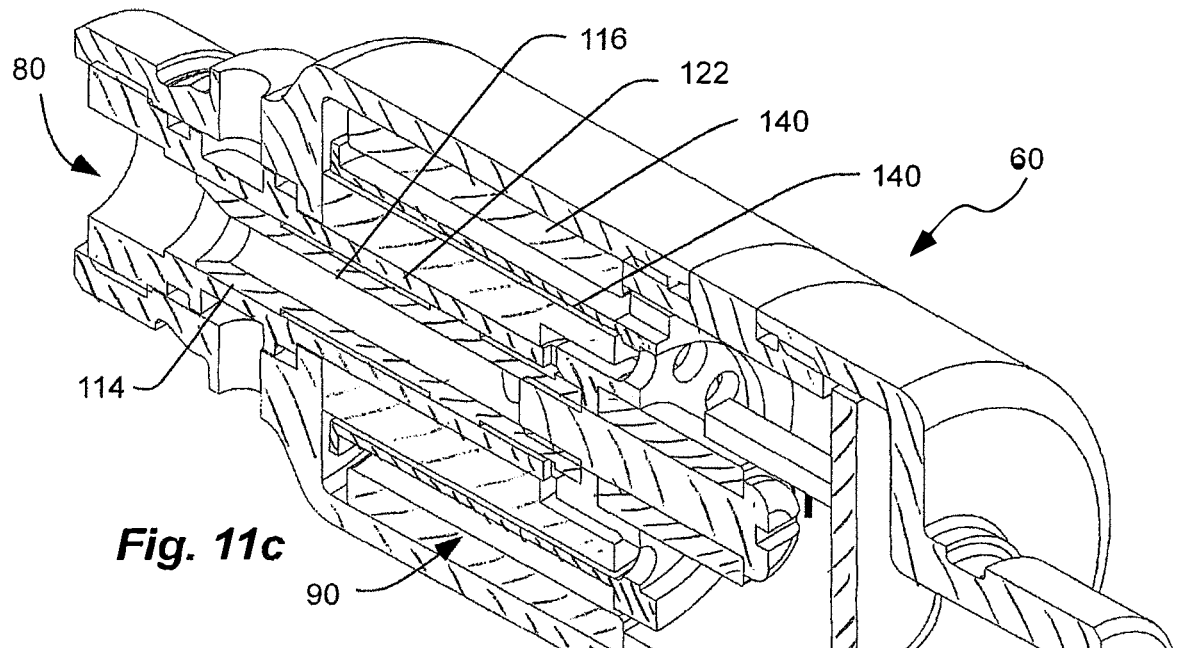
FIG. 11c is a cross-sectional perspective view of the control valve of FIG. 10, taken along line 11a in FIG. 10, and shown in the closed configuration.
Figure 11D:
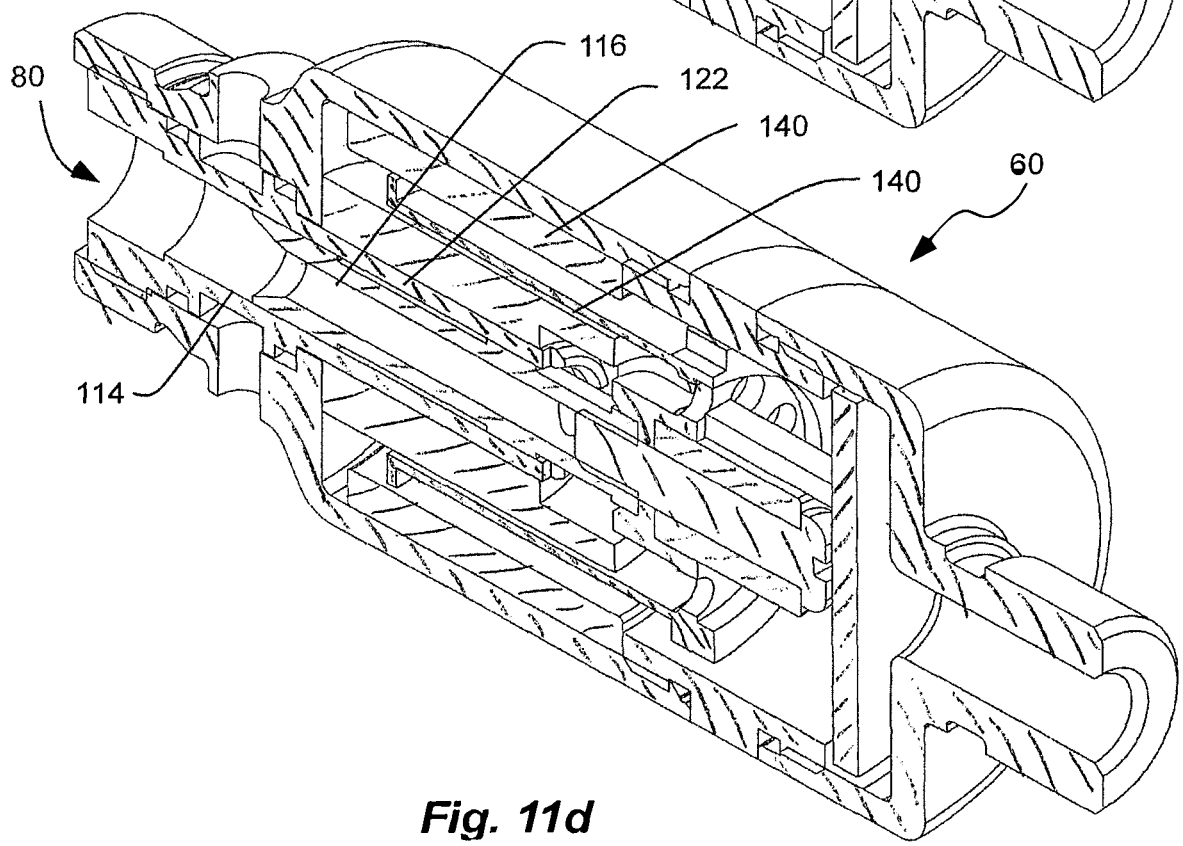
FIG. 11d is a cross-sectional side perspective of the control valve of FIG. 10, taken along line 11a in FIG. 10, and shown in the open configuration.
Figure 11E:
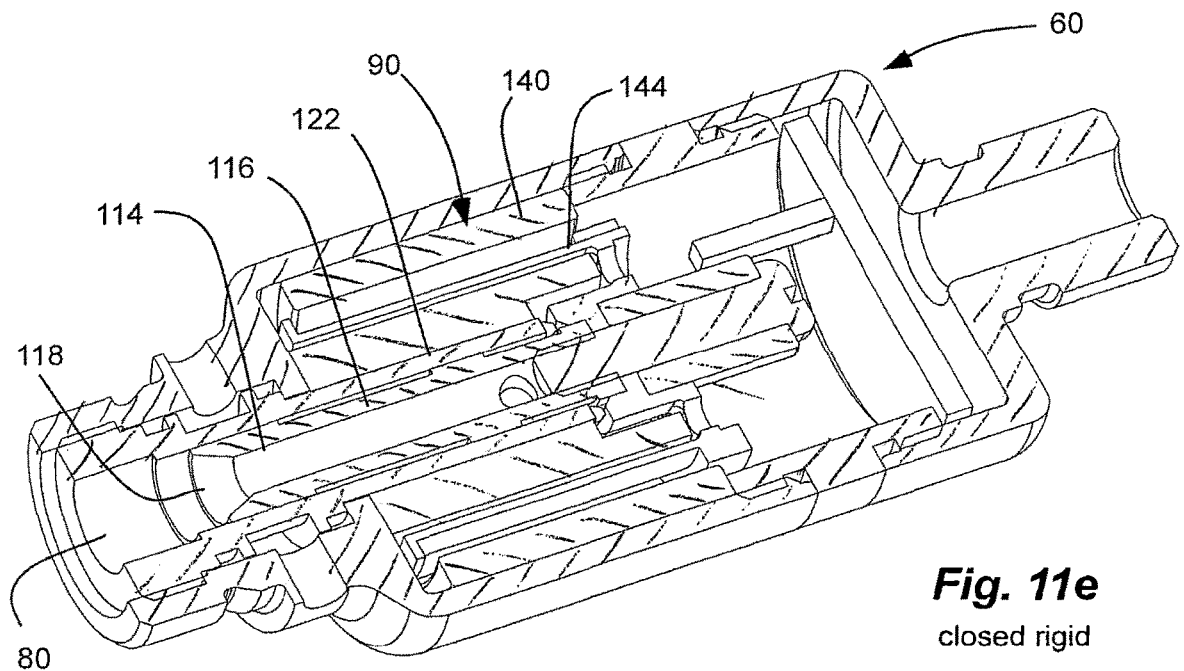
FIG. 11e is a cross-sectional perspective view of the control valve of FIG. 10, taken along line 11a in FIG. 10, and shown in the closed configuration.
Figure 11F:
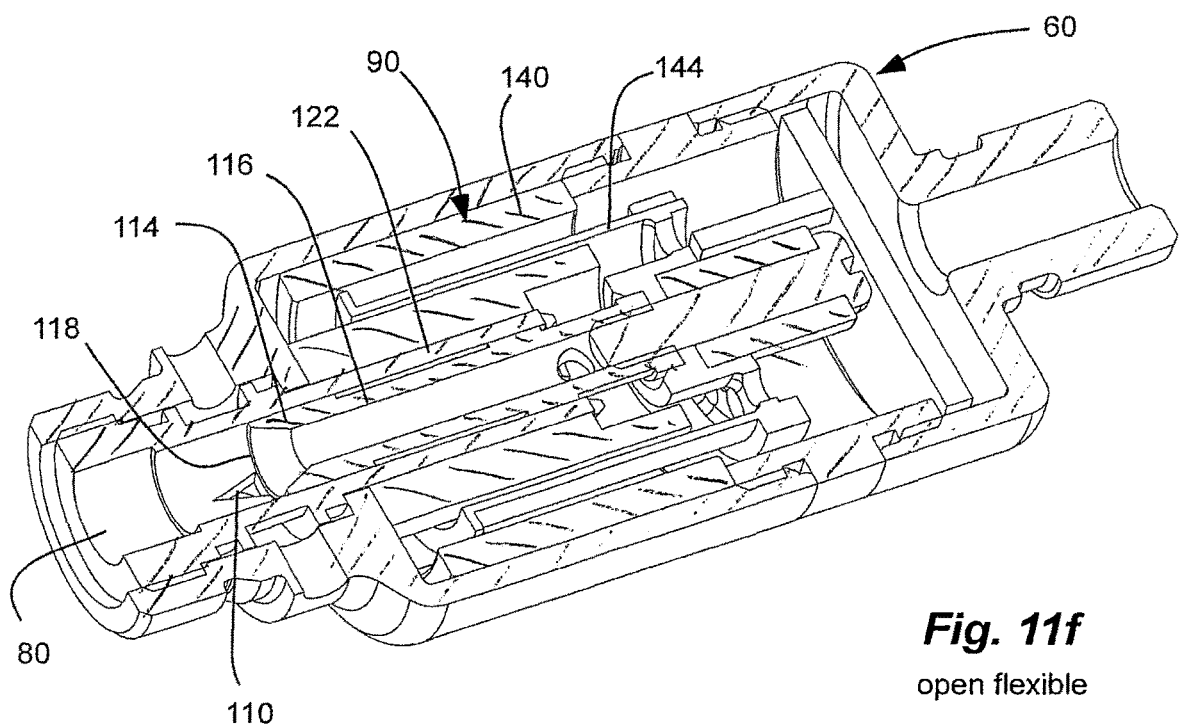
FIG. 11f is a cross-sectional side perspective of the control valve of FIG. 10, taken along line 11a in FIG. 10, and shown in the open configuration.
Figure 13:
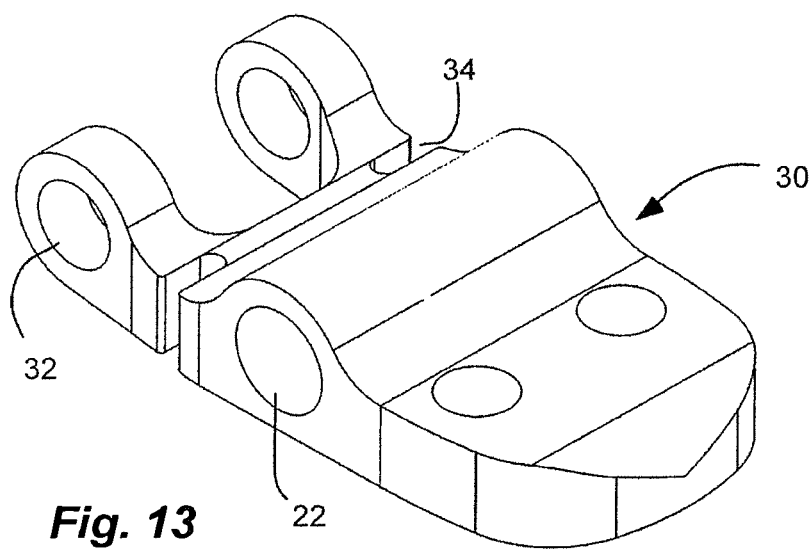
FIGS. 13-15 are perspective, side and top views, respectively, of a flexure based foot coupler mount of the prosthetic ankle of FIG. 1.
Figure 14:
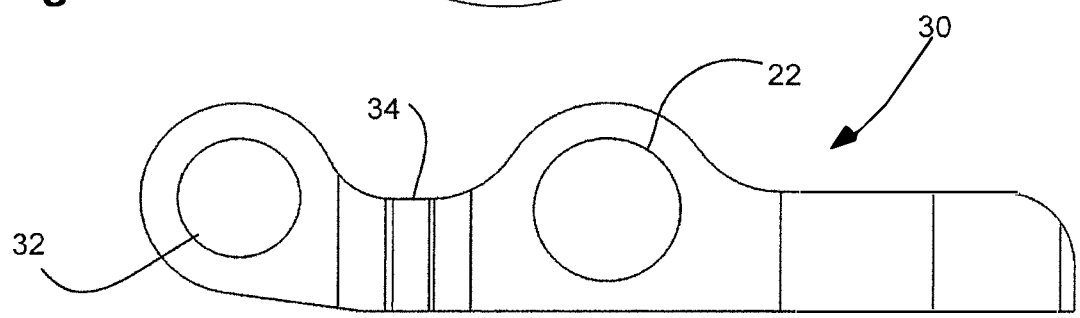
Figure 15:
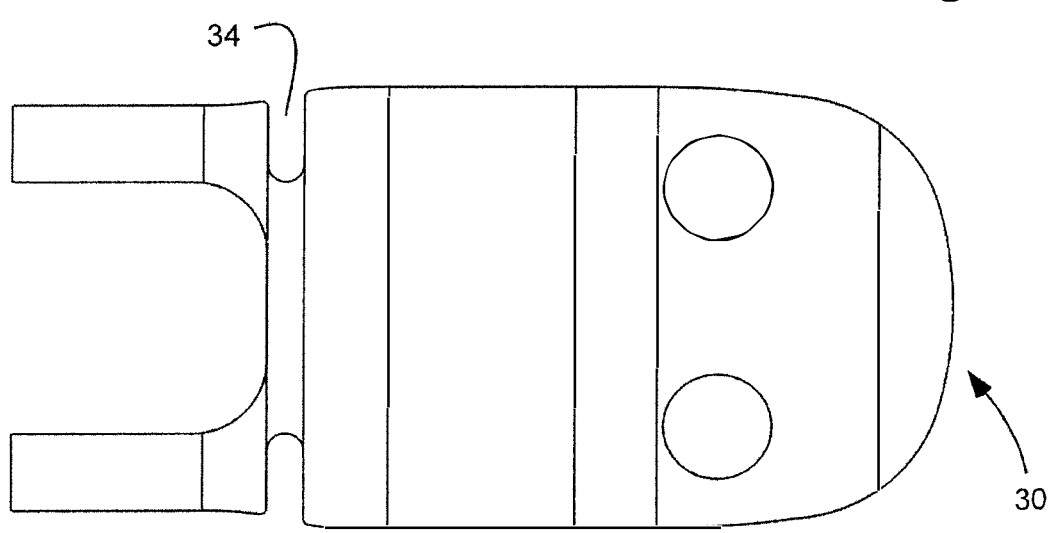

The Figures show the operation of the hydraulic system 40, the hydraulic actuator or damper 50, the control valve 60 or voice coil valve, the hydraulic valve 80 and electric actuator 90. FIGS. 11a, c and e, show the hydraulic system in a locked configuration and the control valve "closed", which can correspond to locking the artificial foot with respect to the shank link. Thus, the artificial foot can lock with respect to the shank link, and the artificial foot can flex or compress under load. FIGS. 11b, d and f show the hydraulic system in a flexible configuration with the control valve "open" or less restricted to have a greater flow rate and a lesser resistance. Thus, the artificial foot can move more rapidly or with lesser resistance. It is noted, however, that the artificial foot can move more slowly and with greater resistance (i.e. with the control valve more "closed" or more restricted) depending on the gait cycle.

Referring to FIGS. 11a, c and e, the control valve 60 is closed; the piston 58 is locked in the cylinder 54; and the artificial foot is locked with respect to the shank link.

Referring to FIGS. 9a-c, 11b, d and f, the control valve 60 is open; the piston 58 can move in the cylinder 54; and the artificial foot can move with respect to the shank link. The hydraulic fluid is displaced by the piston out of one chamber or portion of the cylinder, through the channel 66 and the hydraulic valve 80 (and orifice 110), and into the other chamber or portion of the cylinder. The hydraulic fluid is displaced into the control valve 60 or voice coil valve through and into the sleeve 122, and through and into the spool 114, and to the orifice(s) 110 in the sleeve.

The hydraulic system 40 or the hydraulic actuator or damper 50, or the piston 58, the rod 62 and the cylinder 54 with the control valve 60 or voice coil valve, the hydraulic valve 80 and electric actuator 90 therein, can be provided as a discrete unit that can be removed and installed on the prosthetic ankle. For example, the rod 62 can be coupled to the foot coupler mount 30 and the cylinder 54 or upper cap 70 thereof can be coupled to the shank link 14. In addition, the control valve 60 or voice coil valve, the hydraulic valve 80 and electric actuator 90 therein can be provided as a discrete unit that can be installed in the cylinder and coupled to the piston 58. The control valve 60 or voice coil valve can have a housing 300 (FIGS. 9c and 10) with an open end 304 that can be coupled to the piston 58. (The actuator 90 and the hydraulic valve 80 can be disposed in the housing 300.) The piston 58 can have a receptacle or socket 308 (FIG. 9c) to receive a plug 312 or protrusion in the housing 300 with the open end 304 of the control valve 60. Thus, the piston can carry the control valve. One or more opening(s) can be formed in an opposite side of the piston, opposite from the receptacle or socket 308, and partially defining the flow channel 66. One or more lateral opening(s) 316 can be formed in the housing 300 and spaced-apart from the open end 304. The lateral opening(s) 316 can extend through the housing 300 and to the orifice 110 in the inner tube 122. Thus, the orifice 110 can be disposed between the lateral opening(s) 316 and the open end 304. The lateral openings 316 and the open end 304 can partially define the flow channel 66 through the piston.

The housing 300 can also have an opposite plug 320 or protrusion opposite the piston. The opposite plug 320 can receive a top shaft 324 that can extend through an opening in the top cap 70. The top shaft 324 can have the same diameter and cross-sectional area as the piston rod 62 so match the change in volume on each side of the chamber as the piston moves. The top shaft can form an opposite rod that can be formed on the piston on the opposite side of the piston rod so that the total volume inside the hydraulic cylinder doesn't change as the piston moves. The through rod piston cylinder type hydraulic actuator or damper will require a smaller variable volume 501 or reservoir, with a spring and an independent floating piston (IFP) 503, to operate since the variable volume only compensates for temperature changes and not fluid displaced by the shaft as equal amounts of shaft or rod enter and leave the cylinder at the same time. This also reduces the cycle life requirement of the variable volume since it moves only when the temperature changes, not every time the piston position changes. The variable volume 501 or reservoir can be formed in the piston rod 62, and can include a spring and an independent floating piston (IFP) 503 biased by the spring.

A through rod piston cylinder type hydraulic actuator or damper is used to create a system that can generate high pressure in both the extension and compression directions without a spring bias towards extension. A standard cylinder (rod on only one side of the piston) requires a variable volume to accommodate for the fluid that is displaced by the rod as the cylinder is compressed. If high pressure must be generated in the extension direction of a standard cylinder, then a stiff spring must be used in the variable volume. This stiff spring will tend to force fluid out of the variable volume which will force the shaft out of the cylinder which will extend the cylinder. In the case of this hydraulically controlled ankle, a cylinder spring biased towards extension would result in an ankle that would tend to plantarflex anytime the foot is un-weighted creating a tripping hazard for the amputee.

The through rod cylinder does not need a stiff spring behind the variable volume in order to generate high pressure in both directions if a fixed, small diameter flow orifice 500 is used between the cylinder's main oil chamber or cylinder 54 and the variable volume 501. In high flow situations as would be expected when the piston moves, the pressure drop across the orifice 500 is large, thus the cylinder can generate pressure without moving the spring in the variable volume 501. In low flow situations as would be expected during a temperature change, the pressure drop across the orifice 500 is small, and fluid can move back and forth as necessary between the main oil chamber and the variable volume 501. There are, however, situations where the pressure limit of the cylinder can be exceeded and oil is forced into the variable volume 501 through the orifice. Check valve 502 is placed in parallel to the orifice 500 in order to allow any oil forced into the variable volume 501 immediately back into the main oil chamber. Otherwise, the hydraulic cylinder would develop a dead band.

Thus, an orifice and a check valve are placed in between the chamber where the independent floating piston (IFP) 503 is located and the main oil chamber of a hydraulic cylinder. The orifice permits only low flow between the two chambers. The check valve permits only flow from the IFP chamber to the main oil chamber. With the check valve in parallel with the orifice, the check valve insures that, if a high pressure event forces fluid through the orifice into the IFP chamber, the force of the spring behind the IFP will quickly return that fluid to the main oil chamber through the low resistance path of the check valve once the high pressure event is over. This insures that a high pressure event doesn't cause a long-term "dead band" in the cylinder because the cylinder has effectively lost fluid from the main oil chamber into the IFP chamber. The check valve in parallel with the orifice provides the ability to achieve high pressure in both compression and extension. Without the orifice, either high pressure could be achieved in only one direction, or a very stiff spring would have to be used behind the IFP. A very stiff spring is undesirable because it takes up a lot of space, and in the case of a standard cylinder (shaft on only one side of the piston), it limits the minimum force required to compress the cylinder. In the current invention (microprocessor controlled ankle), we have a through-rod cylinder (shaft on both sides of the piston). The IFP is needed to accommodate volume changes due to temperature changes as well as oil loss over time. Thus the orifice in parallel with the check valve in front of the IFP allows the cylinder to achieve high pressure in both directions while using a reasonably small and compact spring behind the IFP.

Volume compensation in the hydraulic cylinder can be provided in order to allow for the change in the oil volume as the hydraulic cylinder heats up or cools down, and to allow for the change in the volume of the cylinder as compression occurs and the rod enters the cylinder in the case of a cylinder that doesn't have a through rod. The volume compensation can be provided with the independent floating piston (IFP) or a flexible bladder, but can also prevent or resist the hydraulic cylinder from generating high forces in both directions. In the example of a prosthetic ankle that uses a hydraulic cylinder, the ankle may not generate both sufficient plantarflexion (toe going down) resistance and sufficient dorsiflexion (toe going up) resistance. Thus, it can be desirable to isolate the IFP from the main oil chamber with the flow orifice 500, thereby making it possible for the cylinder to generate high forces in both directions while still having volume compensation. In addition, the check valve 502 can be placed in parallel with the flow orifice 501, thereby preventing or resisting oil from getting trapped in the IFP chamber in the case of an over-pressure event. If oil gets trapped in the IFP chamber, it can cause a dead band in the main oil chamber. A dead band in the main oil chamber can be a safety hazard since it creates a region in which the cylinder can move with little to no resistance. Thus, the check valve prevents or resists a safety hazard.

The prosthetic ankle 10 can include a power supply (such as batteries 158) and a control module. In one embodiment, the control module can include a valve controller 160 carried by the hydraulic chamber 54 or hydraulic system, and disposed between the pair of arms of the yoke; and a main controller 162 disposed on both sides of the yoke). The actuator 90 can be electrically coupled to the control electronics and power supply to control and drive the actuator, and thus the operation of the prosthetic ankle.

The prosthetic ankle 10 can also have sensors associated therewith to monitor the ankle, the artificial foot, their relative position, the gait cycle, the hydraulic system, etc. As stated above, the prosthetic ankle can include sensors, such as force or load sensor, torque sensor, angle sensor, accelerometer and/or gyroscope. These sensors can be carried by and disposed on the prosthetic ankle and/or artificial foot itself. For example, a force or load sensor, a torque sensor, or a combination thereof 350, can be disposed on or coupled to the shank link between the shank link and connector to measure force, torque, or both applied by the user to the prosthetic ankle or artificial foot. The force and torque sensor can be an integral part of the connector. The torque sensor can sense ankle torque in the sagittal plane. Various aspects of robust and compact force and torque sensor are found in U.S. Pat. No. 8,746,080 (application Ser. No. 13/015,423, filed Jan. 27, 2011), which is hereby incorporated herein by reference. It is desirable in prosthetic control systems to measure both the vertical force applied to the product and the torque applied in the sagittal plane. Because the torque generates strains that are much greater than those generated by the force, it is difficult to design a single sensor that measures both of these signals. As another example, an angle sensor 354 can be carried by an ankle shaft of the pivot 22 between the shank link and the artificial foot to measure relative angle between the shank link and the artificial foot. As another example, an accelerometer, a gyroscope, or a combination thereof 358 can be carried by a foot coupler mount or the artificial foot to sense or measure impact, orientation, etc. Disposing the sensors on the prosthetic ankle and/or artificial foot allows the prosthetic ankle to be a unitary device without components disposed on other structure, such as pylons. Similarly, locating an angle sensor between the shank link and the artificial foot allows relative orientation to be determined without having to determine a relative orientation of other structure, such as a pylon, and without having to locate sensors on a pylon.

The control system can open the voice coil valve when the artificial foot is un-weighted to allow the artificial foot to pivot with respect to the shank link to allow for terrain adaptation; and can close the voice coil valve when the artificial foot is weighted to lock the artificial foot with respect to the shank link to allow the artificial foot to function. The control system can utilize a control algorithm(s) that can smoothly transitions from a condition where ankle motion comes from both hydraulic cylinder motion and carbon fiber foot deflection, to a condition where the hydraulic cylinder is locked and continued ankle motion comes only from carbon fiber foot deflection. The position at which the hydraulic cylinder locks can be, at a minimum, a function of the patient's preference, the heel height of the current footwear, and/or the slope of the terrain.

The control system can include circuitry configured to enable a compliant ankle whenever the foot is un-weighted. The control system circuitry can be configured to lock the ankle at an appropriate angle based on the position of the foot relative to the shank when weighted. The compliance enables the artificial foot to adapt to different terrain. Locking the ankle allows for typical carbon fiber foot function where the carbon fiber stores energy as the toe is weighted. This stored energy helps propel the foot forward at toe off.

Figure 16:
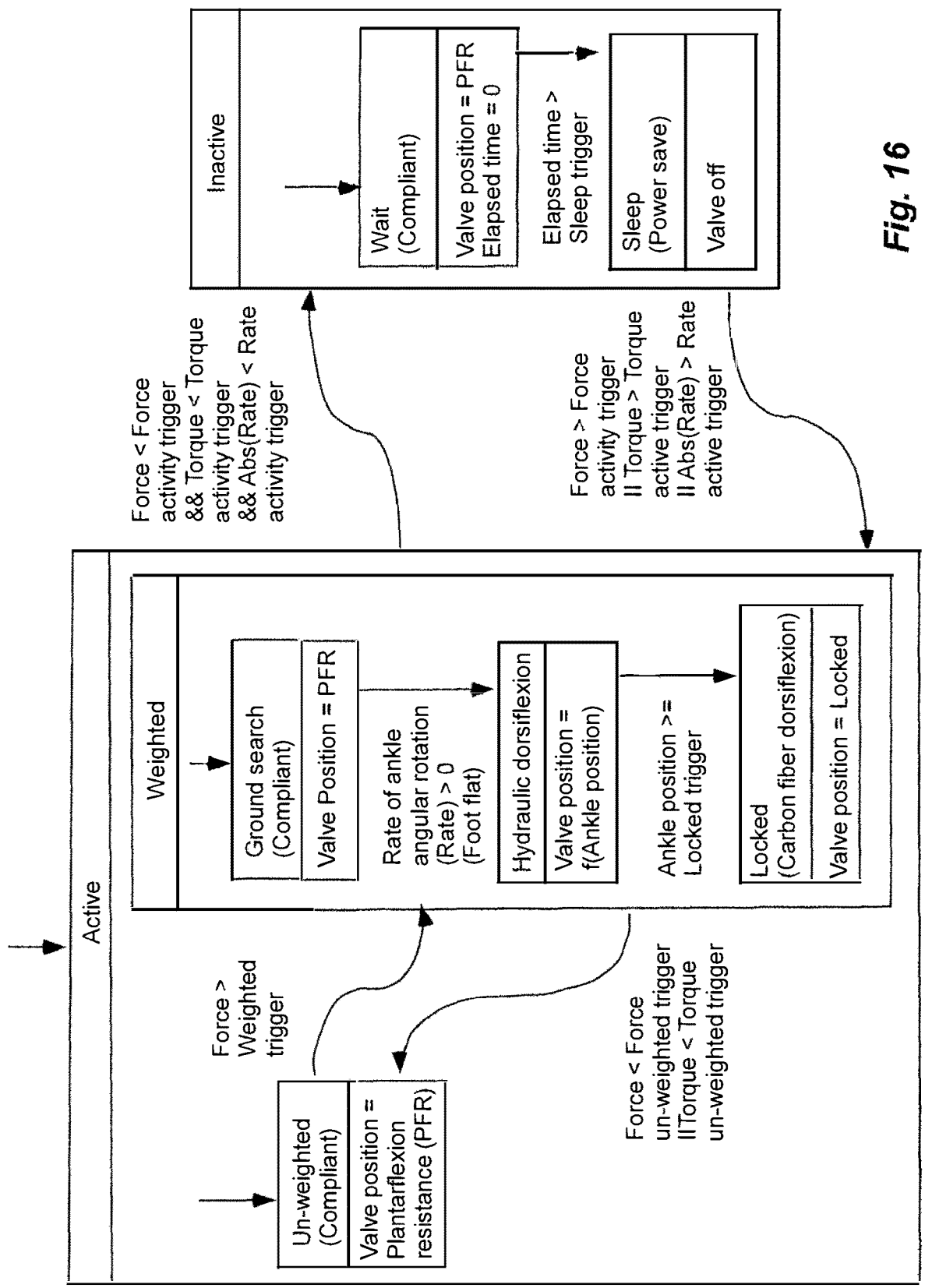
FIG. 16 is a schematic view of the control system of the prosthetic foot of FIG. 1.
Figures 17A, 17B:
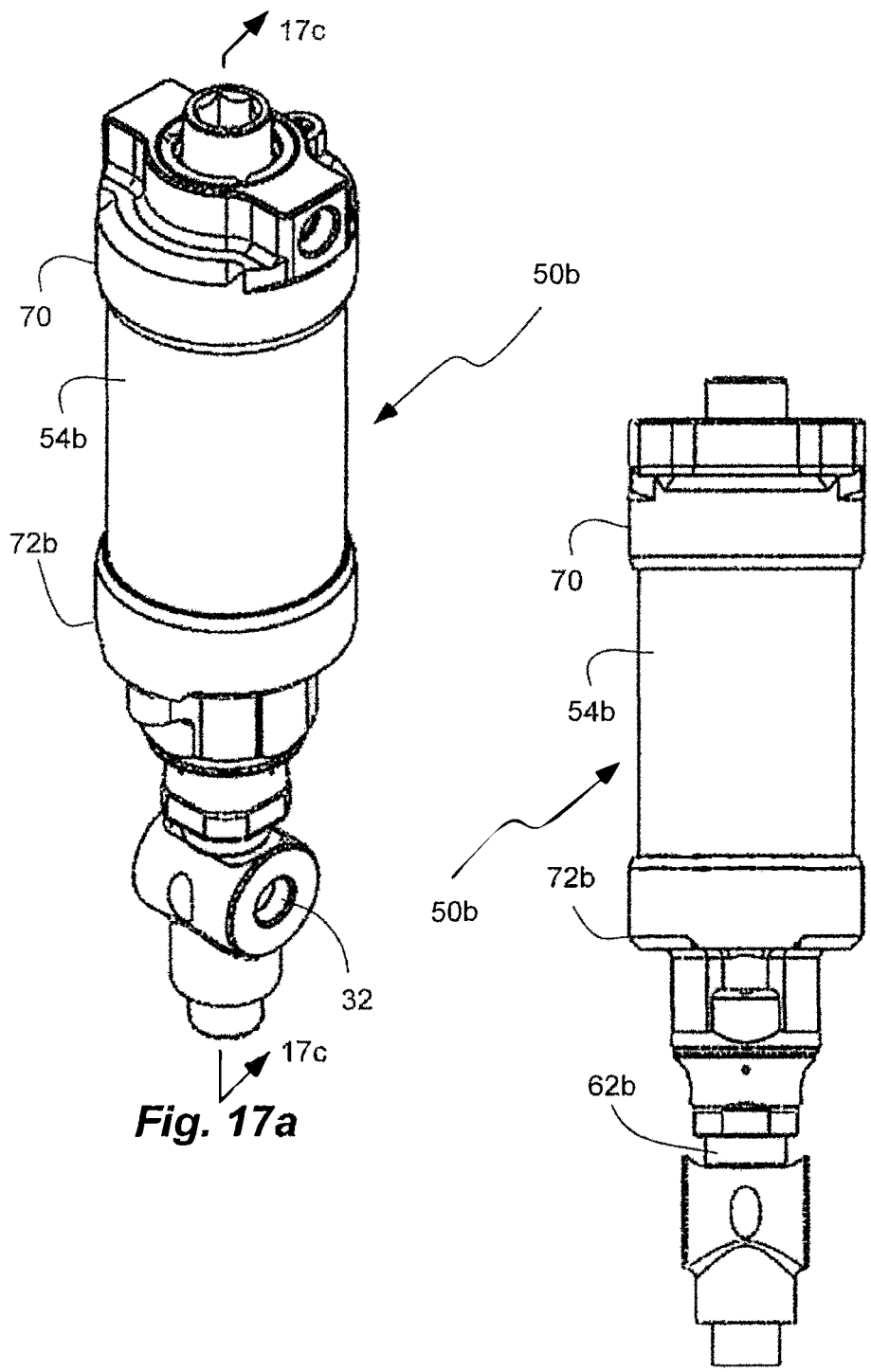
Figures 18C, 18D:
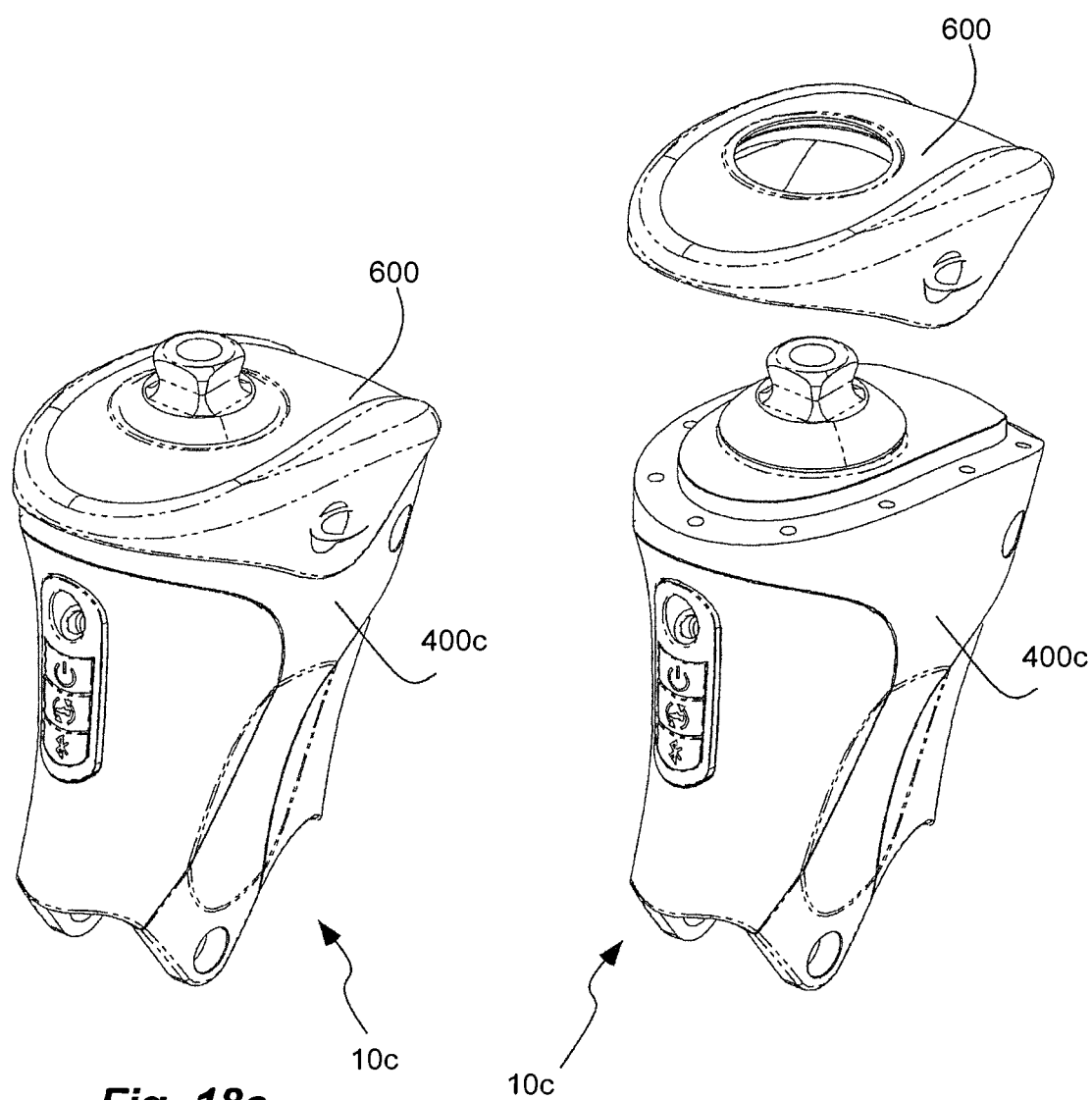
FIG. 18c is a partial perspective view of the prosthetic ankle of FIG. 18a, shown with a cap.
FIG. 18d is a partial, exploded, perspective view of the prosthetic ankle of FIG. 18a, shown with the cap.

Referring to FIG. 16, the control module can initially be set to an un-weighted state as indicated by the arrow with no source state. In the un-weighted state, the valve is opened to allow the ankle to move when the foot makes initial contact with the ground. The amount the valve is open is configurable and is set by the end user to provide a comfortable rate of movement as the foot progresses from initial contact with the ground to being flat on the ground. This is noted in the diagram (FIG. 16) as Valve Position=Plantarflexion Resistance. In another aspect, the plantarflexion resistance selected by the end user can also be dynamically adjusted from step to step by the control system to accommodate, for example, changes in the slope of the terrain, gait speed, etc. The transition from the un-weighted state to the weighted state can be triggered when a configurable force (weight) threshold is exceeded.

The weighted state can include different sub-states. An initial state is a ground search state. The ground search state sets the Valve Position=Plantarflexion Resistance and transitions to the hydraulic dorsiflexion state when the foot is flat on the ground (foot flat). Foot flat can be detected when the rate of hydraulic ankle angular rotation changes in a positive direction, or when ankle movement changes from a negative direction to a positive direction. The foot flat condition can also be detected by looking at ankle torque. In the hydraulic dorsiflexion state and during normal gait, the valve progressively closes over a period of time based on an algorithm. For example, the valve position can be a linear function of the hydraulic ankle position as illustrated by the equation:

$$x = \frac{(x_{CL} - x_{DFR})}{(\theta_T - \theta_{FF})}(\theta - \theta_{FF}) + x_{DFR}, \tag{1}$$

where x=the current valve position,
$x_{CL}$=the valve position at which a valve orifice of the control valve is completely closed,
$x_{DFR}$=the valve position selected by the amputee that produces an amount of initial dorsiflexion resistance (dorsiflexion resistance valve position),
θ=the current ankle position angle,
$\theta_T$=the ankle position angle at which the hydraulic ankle will switch to into a locked state, and
$\theta_{FF}$=an ankle position angle when the foot of the device is flat on the ground (flat foot) or when the device initiates a hydraulic dorsiflexion state.

In another aspect, $x_{DFR}$ can also be modified from step to step by the control system to accommodate, for example, changes in the slope of the terrain, gait speed, etc. Additionally, $\theta_T$ can be determined for each step using:

$$\theta_T = \theta_{HH} + \delta_S + \delta_P, \tag{2}$$

where $\theta_T$=the ankle position angle at which the hydraulic ankle switches to the locked state (trigger angle),
$\theta_{HH}$=a default ankle position angle at which a hydraulic ankle switches to the locked state based on a heel height of the current footwear,
$\delta_S$=an offset angle from the default locked ankle position based on the slope of the terrain, and
$\delta_P$=an offset angle from the default locked ankle position based on user preference.

Thus, the control system changes the position at which the hydraulic resistance is applied based on patient's preference, heel height of the footwear, and/or slope of the terrain using algorithm (2). The sensors for detecting the slope of the terrain and calculating $\delta_S$ for each step can include an inertial measurement unit (IMU, accelerometer and gyroscope), a ankle position sensor to detect an ankle position at foot flat, a torque sensor to determine an amount of torque applied to the ankle, etc.

In another embodiment, the control system can progressively close the valve during the hydraulic dorsiflexion state using an algorithm that employs a non-linear progression from the dorsiflexion resistance valve position to the closed valve position, as opposed to the linear progression described above.

Hydraulic dorsiflexion can transition to the locked state once the ankle position reaches the trigger angle determined using equation (2) in the preceding paragraphs. In the locked state, the valve is commanded to the physical end stop. In one example, the orifice(s) are not only completely closed at the physical end stop, but there is also some spool overlap to reduce the amount of fluid leaking through the valve. In this example, the hydraulic cylinder is then locked and the ankle will not articulate any further. When the ankle will not articulate the foot will act like a traditional carbon fiber foot and provide expected characteristics and performance.

In one configuration, the control system can be configured to transitioning from the weighted state to the un-weighted state only after the patient has removed almost all of his or her weight from the foot. Because the force is very small at this time, noise and/or interference in the force signal can prevent the state transition from occurring at the correct time. Transitioning based on the torque improves the reliability of the transition because, even though the force is small, it is typically applied to the toe of the foot at the time of this transition, and even a small load applied to the toe can create a large torque. In another aspect, the control system can be configured to transition back to the un-weighted state at any time while in the weighted state when the foot becomes un-weighted as detected by the force sensor (weight). The un-weighted trigger is a variable threshold.

Figure 19A:
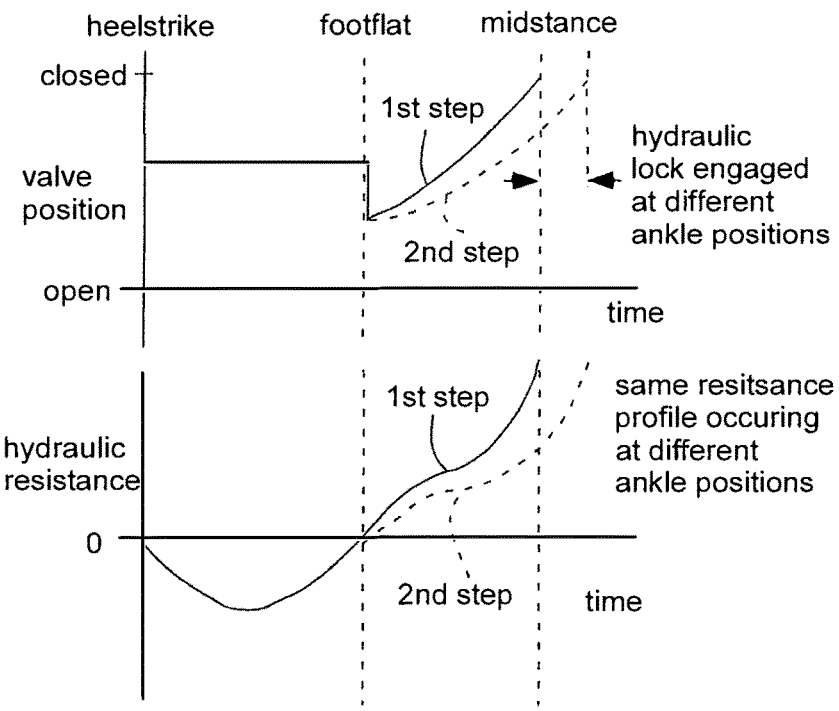
FIG. 19a is a graph of valve position and hydraulic resistance versus time for the prosthetic ankle in accordance with a embodiment of the present invention.
Figure 19B:
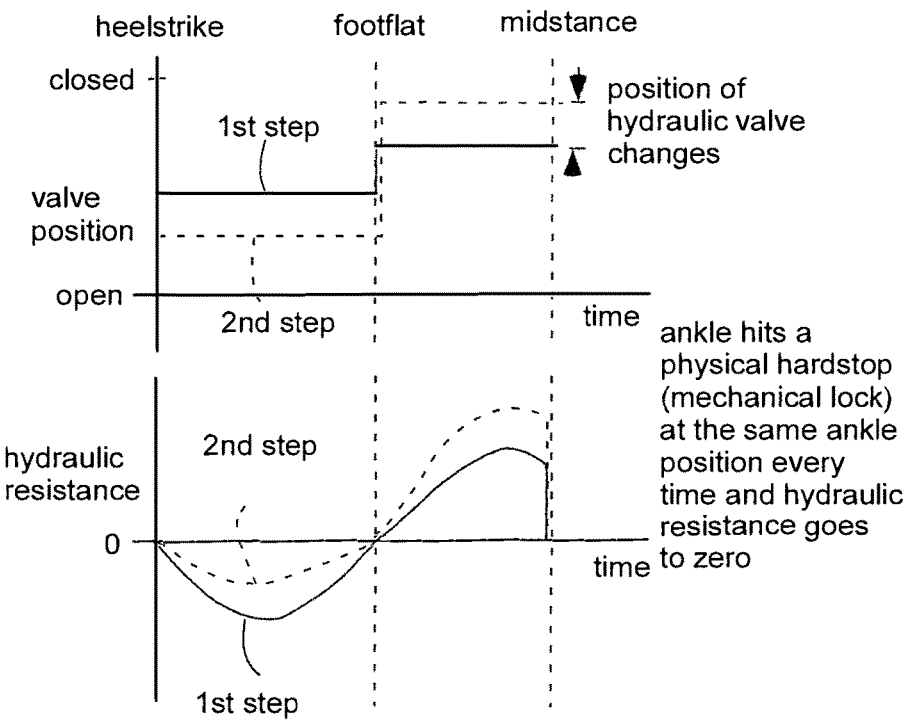
FIG. 19b is a contrasting graph of valve position and hydraulic resistance versus time.

The preceding paragraphs described operation of the control system of a prosthetic ankle that responds reliably and predictably because of the simplicity of the control algorithm, while providing an algorithm that is robust in that a single algorithm works well for level ground, slopes, and stairs. Referring to FIGS. 19a and 19b, the control algorithm can always use the same hydraulic resistance, but change the ankle position (relative angle between the foot and the shank link) at which that hydraulic resistance is applied; as opposed to changing the hydraulic resistance, as shown in FIG. 19b. The control algorithm and/or the control system circuitry can be configured to apply the same hydraulic resistance profile from step to step or from gait cycle to gait cycle, but can also shift the hydraulic resistance profile earlier or later in the step or gait cycle, as shown in FIG. 19a. Thus, the hydraulic resistance profile remains constant from step to step, or over a series of steps, or from gait cycle to gait cycle, but the control algorithm and/or the control system circuitry can be configured to change where in the gait cycle the hydraulic resistance profile is initiated or applied, as shown in FIG. 19a. In addition, the control valve and the control algorithm and/or the control system circuitry can be configured to change a position (ankle position or relative angle between the foot and the shank link) at which hydraulic resistance occurs, as shown in FIG. 19a. Furthermore, a position of a hydraulic lock-out, such as a dorsiflexion stop, can change. Thus, the prosthetic ankle or hydraulic system does not have a hard stop, or a mechanical stop, that is fixed, as shown in FIG. 19b. The hydraulic system can provide the hydraulic lock-out, such as the dorsiflexion stop, and the position at which the hydraulic lock-out or the stop occurs can change. The hydraulic system can provide the hydraulic lock-out or the stop earlier or later in the gait cycle.

While in the un-weighted state, a transition into an inactive state can also occur when a measurement from a sensor, such as a force sensor, a torque sensor or an ankle position sensor, decreases below a configurable threshold based on a detected motion of the foot. In one aspect, the force, torque and ankle position sensors can be utilized. In another aspect, transition into the inactive state can occur when the output of the IMU decreases below a configurable threshold set to detect motion of the foot. The combination of the force, torque, and ankle position sensors used by the control system uses less power than the IMU. Thus, the force, torque and ankle position sensors can be on in the low power sleep state, instead of the IMU. In addition, utilizing the force, torque and ankle position sensors can provide a more reliable transition between the inactive state and the active state because the ankle position sensor can detect if the hydraulic ankle is moving, while the IMU can only detect if the entire foot is moving. In addition, the force and torque sensors give subsequent information about whether or not the user or patient has weight on the prosthetic ankle. Furthermore, using both force and torque information to switch between the inactive state and the active state can provides more reliable behavior. In one example, when the control system is in the inactive state, a small force could be applied to the toe of the foot while the hydraulic ankle is against the dorsiflexion stop. In this case, the force may not exceed the trigger set to transition back into the Active state, and the ankle position sensor would not detect any movement because it is already against the dorsiflexion stop; consequently, the torque would exceed the trigger set to transition back into the Active state. The wait state is initiated upon entering the inactive state. The transition to the sleep state occurs after the elapsed time since entering the wait state is greater than a configurable time limit. When the control algorithm has entered a sleep state, the valve is turned off to save energy and improve battery life. Other possible energy saving activities in the sleep state include: turning off other electronic systems (sensors, etc.) to save energy; going into a deep sleep state after another time delay.

Having a low power "sleep" state (dependent on the force, torque, and ankle rate of rotation) allows the prosthetic ankle to have a smaller battery pack. In addition, the battery pack can be internal to the prosthetic ankle. It can be undesirable to have a large external battery pack that is attached via a tether and must be mounted to the outside of the prosthetic socket. This creates more work for the clinician to mount the battery pack on the socket, causes reliability issues for the patient when the tether fails, and makes the prosthetic leg look unnatural because it has a battery pack attached to it.

The control system can include a connection via Bluetooth 1.0, 2.0, 3.0, or 4.0 (classic, high speed) and/or Bluetooth Low Energy (low speed) with a communications protocol that contains many networking standard elements, such as packet sequencing and checksums. The control system or controller can wirelessly connect to a user interface with a pair of transceivers, each one carried by a different one of the prosthetic (and operatively or electrically coupled to the controller) and the user interface, and wirelessly connecting the user interface and the controller. The user interface can include a computing device with a user input, such as a tablet computer with a touch screen, a laptop computer, a desktop computer with a monitor, a cellular phone or smart phone, etc. A wireless connection between the user interface and the product is highly desirable in electronic prosthetic products. It allows the patient to move around freely unobstructed by wires while the prosthetist can easily make adjustments to the product on-the-fly or see information coming from the product. However, an unreliable wireless connection can be more bothersome than the restrictions of a wired system. In addition, the control system can, under the control of one or more computer systems configured with executable instructions, open or begin a "session". During a session, information about the prosthetic can be sent by the controller to the user interface, including for example, force, loads, torques and slopes measured me the sensors; gait information such as gait cycle; hydraulic information such as hydraulic pressure, valve position, and power consumption; locking and unlocking positions of the valve with respect to gait cycle or foot angle; battery level and output; etc. In addition, during a session, control information or commands can be sent to the controller, including for example, user preferences on heel height, position of locking and unlocking of the valve; the ankle position at which the hydraulic ankle will trigger into the locked state; the default ankle position at which the hydraulic ankle will trigger into the locked state as determined by the heel height of the current footwear; an offset to the default locked ankle position based on the slope of the terrain; an offset to the default locked ankle position based on user preference; etc. A session begins upon the first connection and continues until the application is closed. If a wireless connection is broken (likely due to a weak signal) the software will automatically attempt to reconnect for a period of time. If a reconnection is made, the previous state of the session will resume where it left off or at the point of termination. In many cases, the user may not even know that the connection had been broken and then re-established. The purpose of this mechanism is to create a seamless experience for the user, even if/when the patient walks out of range for brief periods of time. The session allows the wireless connection to be momentarily interrupted with minimal impact. Most of the time, the prosthetist may not even know the wireless connection was even interrupted. This provides for a more positive user experience.

As stated above, and referring to FIGS. 12a-c, the ankle can include a housing 400 that can be disposed around a majority of the ankle. The housing 400, the shank link 14 and the artificial foot 18, and the hydraulic actuator or damper 40, can be disposed in an anatomical envelop of a natural leg. The control system and the battery can be disposed in the housing. Thus, the control system and the battery can be disposed in an anatomical envelop of a natural leg.

Referring to FIGS. 17a-17d, another hydraulic actuator or damper 50b is shown that is similar in many respects to that described above, and which description is hereby incorporated herein by reference. The hydraulic actuator or damper 50b includes a mechanical ball lock 450 as part of the prosthetic ankle or joint to lock or lockout the prosthetic ankle or joint, and is an integral or integrated part of the hydraulic cylinder. Thus, the need for a separate mechanism to provide locking is avoided, making the prosthetic ankle compact and lightweight.

As described above, the mechanical ball lock can lock the prosthetic ankle. The prosthetic ankle can have a large range of motion (e.g. 30 degrees), and can provide many advantages (such as comfort while sitting, the ability to use footwear with high heels, the ability to go up and down steep hills or ramps, etc.). In addition, the large range of motion and/or the hydraulic system can also pose a safety risk. The mechanical lock can be engaged by the patient to mitigate safety risks. The mechanical lock can be used to improve safety in the case of a system failure such as a dead battery, a broken wire, etc. It can also be used to improve safety in situations where the patient would not want any unexpected ankle motion to occur, such as driving a car, climbing a ladder, etc. In addition to improved safety, the mechanical lock can also provide convenience for the clinician. The clinician can lockout the ankle during dynamic alignment of the prosthetic leg using the mechanical lock. This allows the clinician to focus on the alignment without having to worry about the hydraulic settings at the same time.

The mechanical ball lock 450 can be carried by a piston rod 62b of the hydraulic piston 58, and can releasably engage with the hydraulic chamber or cylinder 54b, to lock the hydraulic piston and the hydraulic chamber with respect to one another. A collar 454 can be rigidly affixed to the hydraulic chamber or cylinder 54b. The collar can extend from the cylinder and can have an axial bore or through hole therein for slidably receiving or concentrically receiving the piston rod 62b. The collar can extend from the lower cap 72b, or can be formed integrally with the lower cap 72b, of the chamber or cylinder. In addition, the collar or interior thereof can have an indentation 458 therein. The indentation 458 can be an annular groove circumscribing an interior or the collar, and the piston rod. The piston rod 62b extends through the collar 454 and hollow thereof. In addition the piston rod 62b has a hollow or axial hollow therein, and at least one hole 462 therethrough. The hole 462 can extend laterally or radially through the piston rod or wall thereof. In one aspect, the hole can comprise four holes. At least one ball 466 is movably disposed in the at least one hole 462 of the piston rod. The at least one ball 466 can move concentrically in the direction of the at least one hole 462. In one aspect, the ball can comprise four balls. In normal operation of the prosthetic ankle, the ball(s) can reside in the hole(s), as shown in FIG. 17d. When the ball lock 450 is operated, the ball(s) an extend partially out of the hole(s) and partially into the indentation 458 or annular groove in the collar 454 to lock the collar and the piston rod with respect to one another, and thus the piston and chamber or cylinder with respect to one another, as shown in FIG. 17c. An engagement pin or plunger 470 can be movably disposed in the hollow of the piston rod 62b. The pin or plunger can have an enlargement 474 to displace the at least one ball partially into the indentation in the interior of the collar when the indentation is aligned with the at least one hole so that the at least one ball is in both the at least one hole and the indentation to lock the piston rod and the collar with respect to one another, as shown in FIG. 17c. In addition, the pin or plunger can have a reduction or reduced portion 478 that receives or partially received the ball(s) therein in the normal operation of the prosthetic ankle, as shown in FIG. 17d. The pin or plunger can have a first position corresponding to the normal operation of the prosthetic ankle, in which the reduction or reduced portion aligns with the indentation 458 or annular groove in the collar 454, and allows the ball(s) to move out of the indentation 458 or annular groove in the collar 454, and defining an unlocked position. The pin or plunger can have a second position corresponding to and defining a locked position, in which the ball(s) and the hole(s) are aligned with the indentation 458 or annular groove in the collar 454, and the enlargement is aligned with indentation 458 or annular groove in the collar 454. A spring can bias the pin or plunger in the locked configuration when the lock is engaged for safety purposes. In addition, the pin or plunger can be retained in the unlocked position until engaged. In one aspect, the pin or plunger can be positively retained, such as with a pin, a set screw, or the like.

Referring to FIGS. 18a-d, another prosthetic ankle 10c and foot is shown that is similar in most respects to that described above, and which description is hereby incorporated herein by reference. The prosthetic ankle has optional, interchangeable cap 600 and snap-on bond ring 604 removably coupled to the housing 400c. For users or patients that do not want to cosmetically finish the prosthetic ankle (i.e. make it have the shape of a natural leg), the cap 600 can be attached to the top of the housing. The cap can be attached with a snap fit. For users or patients that want to cosmetically finish the prosthetic ankle (i.e. make it have the shape of a natural leg), the snap-on bond ring 604 is removably attached to the housing 400c. A foam cover 608 can be bonded to the bond ring 604 that has the shape of a natural leg. The user or patient can then pull a stocking or sock over the prosthetic ankle, foot and foam cover to look like a natural leg. The bond ring 604 has a flat surface on the top to make it easy to bond foam to. It can be difficult to cosmetically finishing a prosthetic ankle with 30 degrees of ankle motion because of the lack of foam materials that can endure the stretching and compressing that would be necessary if the foam were attached to the top of the foot shell as is typical with a rigid carbon fiber foot with no hydraulic ankle. The foam can quickly break down and needs to be replaced. Thus, the foam cover can be attached to the top of the prosthetic ankle, thereby avoiding the stretching and compressing of the foam when the ankle moves. Attaching the foam cover to the top of the prosthetic ankle instead of the foot shell also has the advantage that it makes it easy to remove and/or replace the prosthetic ankle if needed, for example, in the case when the ankle needs to be repaired. Instead of cutting into the foam, the foam can simply be separated from the ankle by snapping off the bond ring.

In addition, the battery of the prosthetic foot can be charged using electromagnetic resonant wireless charging to allow patients to charge their prosthetic without taking off their prosthetic leg or removing a battery pack for charging. It also facilitates hands-free, worry-free charging. For example, a charging transmitter could be mounted below a couch at home, a car seat, and a chair at the office so that every time the patient sits in one of these locations, the prosthetic leg starts charging automatically with no input from the patient. It would also allow bilateral amputees to charge both prosthetic legs at the same time. In addition, many patients prefer to cover their prosthetic leg with foam to make it have the same shape and size as a natural leg. This makes it difficult or impossible to access charging points or battery compartments. This technology would allow battery charging through the foam cover.

A single or multiple electromagnetic resonant transmitter(s) or source can be tuned to two or more devices as a primary power source, without the need of being spatially aligned to the receiver or coil or power capturing devices. An oscillating magnetic field produces an electric field and an oscillating electric field produces a magnetic field. Inductive chargers, such as those found commonly in electric toothbrushes, operate on the principle of electromagnetic induction. However, for these systems to operate efficiently, the primary coil (source or transmitter) and secondary coil (receiver or power capture device) must be located in close proximity and carefully positioned with respect to one another. This method enforces a limitation of tight spatial alignment of the power transmitter to the power receiver for delivering the power. In addition, the close proximity requirements of the power transmitter to the integrated power receiver can be cumbersome for an amputee as it could limit mobility or natural motion of limbs while sitting or standing, etc. Strategically placed multiple magnetic resonant transmitters or sources in the routine pathways of an amputee—in a home or office environment, shall allow perpetual charging of the battery powered limb as they freely walk around—possibly eliminating the complete loss of power to their battery powered prosthetic limbs. This charging method could allow amputees to safely charge their battery powered devices while driving a vehicle, virtually eliminating the risk of attached power cords (e.g. car charger) interfering with their foot work activity.

The Electromagnetic Resonant Charging method overcomes the limitations of spatial alignment and articulation restriction of battery powered prosthetic limbs as the power transmitter or source can be placed independent of spatial alignment to the receiver or power capture source with a proximity distance much larger than the inductive charging method.

The charging method employs the wirelessly powered, magnetically coupled, and resonantly tuned transmitter(s) and receiver(s). Magnetic coupling occurs when two objects exchange energy through their varying or oscillating magnetic fields. Resonant coupling occurs when the natural frequencies of the two objects are approximately the same.

Power sources and capture devices are specially designed magnetic resonators that efficiently transfer power over large distances via the magnetic near-field. These proprietary source and device designs and the electronic systems that control them support efficient energy transfer over distances that are many times the size of the sources/devices themselves.

It should be understood that many of the functional units described in this specification have been labeled as modules, in order to more particularly emphasize their implementation independence. For example, a module can be implemented as a hardware circuit comprising custom VLSI circuits or gate arrays, off-the-shelf semiconductors such as logic chips, transistors, or other discrete components. A module can also be implemented in programmable hardware devices such as field programmable gate arrays, programmable array logic, programmable logic devices or the like.

Modules can also be implemented in software for execution by various types of processors. An identified module of executable code can, for instance, comprise one or more physical or logical blocks of computer instructions, which can, for instance, be organized as an object, procedure, or function. Nevertheless, the executables of an identified module need not be physically located together, but can comprise disparate instructions stored in different locations which, when joined logically together, comprise the module and achieve the stated purpose for the module.

Indeed, a module of executable code can be a single instruction, or many instructions, and can even be distributed over several different code segments, among different programs, and across several memory devices. Similarly, operational data can be identified and illustrated herein within modules, and can be embodied in any suitable form and organized within any suitable type of data structure. The operational data can be collected as a single data set, or can be distributed over different locations including over different storage devices, and can exist, at least partially, merely as electronic signals on a system or network. The modules can be passive or active, including agents operable to perform desired functions.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A prosthetic device, comprising:
   a pair of prosthetic members, comprising a shank link configured to be coupled to a remnant limb of an amputee, movably coupled together to allow movement of the pair of prosthetic members with respect to one another;
   a hydraulic actuator or damper including hydraulic fluid in a hydraulic chamber coupled to one of the pair of prosthetic members, and a single hydraulic piston movably disposed in the hydraulic chamber and coupled to another of the pair of prosthetic members;
   a hydraulic flow channel fluidly coupled between opposite sides of the chamber to allow hydraulic fluid to move between the opposite sides of the chamber during movement of the pair of prosthetic members as the hydraulic piston moves therein; and
   a voice coil valve coupled to the hydraulic flow channel to vary resistance to flow of hydraulic fluid through the flow channel, wherein the voice coil valve is positioned within the hydraulic chamber;
   wherein the hydraulic actuator or damper further comprises a floating piston, and wherein a variable volume chamber is formed between the floating piston and the hydraulic chamber.

2. The prosthetic device in accordance with claim 1, wherein the voice coil valve opens or closes flow of hydraulic fluid through the flow channel, and thus allows or disallows movement of the piston in the chamber, and thus unlocks or locks movement of the pair of prosthetic members with respect to one another.

3. The prosthetic device of claim 1, further comprising an artificial foot that is pivotally coupled to the shank link, and wherein the prosthetic device further comprises a flexure mounting the hydraulic actuator or damper to the shank link or the artificial foot, and having a high stiffness in a direction parallel to a line-of-action of the hydraulic chamber to effectively transmit forces to and from the chamber, and having a low stiffness in at least one direction perpendicular to the line-of-action to resist side loads from being transmitted to the chamber.

4. The prosthetic device of claim 3, wherein the shank link further comprises:
   a yoke with a pair of arms extending towards and coupled to the artificial foot; and
   wherein the voice coil valve and the hydraulic actuator are at least partially disposed between the pair of arms of the yoke.

5. The prosthetic device of claim 3, further comprising:
   a foot coupler mount attached to the artificial foot, and wherein the shank link further comprises a yoke with a pair of arms extending towards and pivotally coupled to the foot coupler mount at a single-axis pivot;
   a force sensor, or a torque sensor, or both carried by the prosthetic device or a connector thereof to measure force, torque, or both applied by the user to the prosthetic device or artificial foot;
   a gyroscope, or an accelerometer, or both carried by the foot coupler mount or the artificial foot;
   an angle sensor carried by a device shaft of the pivot to measure relative angle between the shank link and the artificial foot; and
   a control system operatively coupled to the voice coil valve and the sensors and configured with instructions to:
   i) open the voice coil valve when the artificial foot is un-weighted to allow the artificial foot to pivot with respect to the shank link to allow for terrain adaptation;
   ii) close the voice coil valve when the artificial foot is weighted to lock the artificial foot with respect to the shank link to allow the artificial foot to function.

6. The prosthetic device of claim 1, further comprising:
   a housing carried by the shank link and surrounding at least a portion of the shank link;
   a control system disposed in the housing; and
   a battery electrically coupled to the control system and disposed in the housing;
   wherein the housing is configured to fit within an anatomical envelope of a natural leg.

7. The prosthetic device of claim 6, wherein the housing, the shank link, and the hydraulic actuator or damper are configured to fit within the anatomical envelope of a natural leg.

8. The prosthetic device of claim 1, wherein:
the voice coil valve is disposed in and carried by the piston, and movable with the piston inside the hydraulic chamber; and
the hydraulic channel extends through the piston.

9. The prosthetic device of claim 1, wherein the voice coil valve has a rapid response rate, capable of greater than 100 cycles per second, and a low power consumption less than 1.8 Watts.

10. The prosthetic device of claim 1, wherein the voice coil valve further comprises:
   a) a spool defining an inner flow channel;
   b) a sleeve circumscribing the spool;
   c) at least one orifice in the sleeve; and
   d) the spool slidable with respect to the sleeve and the at least one orifice, and having a distal end selectively positioned with respect to the at least one orifice.

11. The prosthetic device of claim 1, wherein the voice coil valve has a coil and a spool with a path of travel parallel with a path of travel of the piston.

12. The prosthetic device of claim 1, wherein the hydraulic actuator or damper further comprises an orifice and a check valve fluidly coupling the hydraulic chamber and the variable volume chamber.

13. The prosthetic device of claim 12, wherein the check valve permits flow from the variable volume chamber into the hydraulic chamber.

14. The prosthetic device of claim 12, wherein the orifice and the check valve are in parallel.

\* \* \* \* \*